United States Patent [19]
Borror

[11] 3,954,799
[45] May 4, 1976

[54] PROTONATED INDOLE PHTHALIDES AND NAPHTHALIDES

[75] Inventor: Alan L. Borror, Lexington, Mass.

[73] Assignee: Polaroid Corporation, Cambridge, Mass.

[22] Filed: Sept. 4, 1973

[21] Appl. No.: 393,798

Related U.S. Application Data
[63] Continuation of Ser. No. 108,662, Jan. 21, 1971, abandoned.

[52] U.S. Cl.................... 260/326.12 R; 252/300; 252/408; 260/326.34; 260/343.2 R; 260/343.3 R
[51] Int. Cl.².................................. C07D 209/12
[58] Field of Search.......... 260/326.13 R, 326.12 R

[56] References Cited
UNITED STATES PATENTS
3,804,855    4/1974    Farber................... 260/326.14 R Primary Examiner—Raymond V. Rush
Attorney, Agent, or Firm—Sybil A. Campbell

[57] ABSTRACT

This invention relates to protonated compounds of the formula:

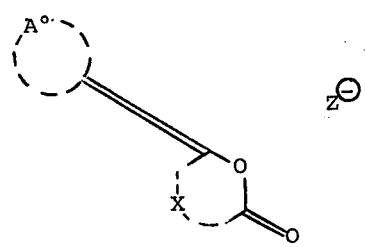

wherein A is a radical selected from

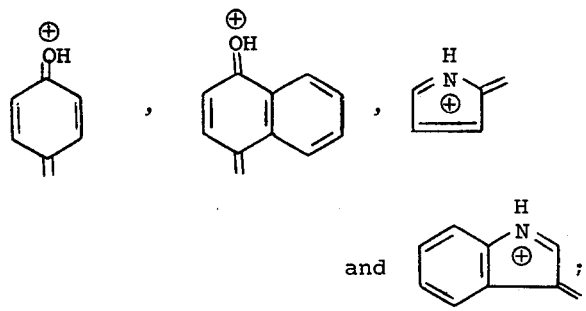

X represents the atoms necessary to complete a ring-closing moiety selected from phthalide and naphthalide; and Z is an anion derived from a protic acid. These compounds are useful as intermediates in the preparation of phthalide and naphthalide indicator dyes.

12 Claims, No Drawings

PROTONATED INDOLE PHTHALIDES AND NAPHTHALIDES

CROSS-REFERENCE TO RELATED APPLICATIONS

This application is in part a continuation of copending application Ser. No. 108,662 filed January 21, 1971, now abandoned.

BACKGROUND OF THE INVENTION

1. Field of the Invention

This invention relates to protonated compounds useful as intermediates in the preparation of phthalide and naphthalide indicator dyes.

2. Description of the Prior Art

Dyes which undergo a change in spectral absorption characteristics in response to a change in pH are well known in the art and are frequently referred to as indicator or pH-sensitive dyes. Typically, these dyes change from one color to another, from colored to colorless or from colorless to colored on the passage from acidity to alkalinity or the reverse and are commonly employed in analytical chemical procedures to measure changes in pH value. Among the indicator dyes most widely used is the group derived from phthaleins as exemplified by phenolphthalein, thymolphthalein, o-cresolphthalein and 1-naphtholphthalein.

Various methods are known in the art for preparing phthalein indicator dyes. In one of the more conventional procedures, phenols, such as thymol, o-cresol, and phenol itself are reacted with phthalic anhydride at elevated temperatures in the presence of a suitable catalyst such as zinc chloride or sulfuric acid to yield the corresponding symmetrical, i.e., di-phenol phthalein. Di-indole phthaleins also have been prepared by simple condensation usually in the presence of an acid catalyst and by other methods, such as, reacting magnesium indyl bromide with phthalyl chloride in accordance with the procedure reported by B. Oddo, Atti accad. Lincei [vi] 1, pp. 236-8 (1925).

Another method of synthesizing indole phthaleins is disclosed in British Pat. Nos. 1,160,940; 1,161,386; 1,161,387; and 1,162,771, which comprises reacting an indole with phthalic anhydride in the presence of a metal halide, e.g., aluminum chloride to yield a keto-acid intermediate which is subsequently reacted with a second aromatic compound, the same or different, in the presence of an acid condensing agent to yield the desired indole phthalein. Using this method both symmetrical and unsymmetrical compounds may be prepared by selecting respectively, as the second aromatic compound, an indole which is the same or an indole which is different from the starting indole initially reacted with the anhydride. Where it is desired to produce a mixed indole phthalein containing an indole radical and a second radical derived from a different aromatic compound such as carbazole or aniline the keto-acid intermediate may be formed by reaction of the indole, carbazole or other appropriate compound with phthalic anhydride followed by condensation of the intermediate with the second aromatic compound to yield the desired mixed indole indicator dye.

These prior methods of preparing phthaleins, though useful in synthesizing a large number of compounds, are accompanied by certain drawbacks. This simple condensation reactions and the Grignard reactions are not useful with all starting materials. Some phenols and indoles will not react under the condensation conditions conventionally employed. Moreover, these synthetic methods generally are limited to the production of symmetrical compounds, i.e., di-phthalides containing two indole or two phenol radicals that are identical. While the method of the aforementioned British patents is useful for producing symmetrical and unsymmetrical indole phthaleins and also mixed indole indicator dyes, the more sensitive indole derivatives, when used as starting materials, tend to decompose under the vigorous reaction conditions encountered in the presence of the aluminum chloride catalyst.

It is known from the work of Brubaker, et al., J. Amer. Chem. Soc., 49, 2279 (1927) that o-phthalaldehydic acid condenses with phenol and certain substituted phenols having a free para-position to yield the para-condensation products. These compounds were prepared by mixing equimolar proportions of phenol and phthalaldehydic acid and then adding a suitable condensing acid, such as sulfuric acid, while maintaining the reaction temperature below about 30°C.

As reported by Norland, et al., ibid., 82, 5143 (1960), phthalaldehydic acid and indoles will condense to yield phthalidylindoles and water when the two reactants are fused together at temperatures of 120° to > 200°C. If the 3-position of the indole is free, then 3-phthalidylindoles are formed. If the 3-position is blocked or if the 1- and 3-positions are blocked, then 1-phthalidylindoles and 2-phthalidylindoles are formed, respectively.

Rees, et al., J. Chem. Soc., pp. 680–687 (1965) observed that for reaction with phthalaldehydic acid the 3-substituted indoles and the 1,3-disubstituted indole generally require the vigorous fusion conditions used by Norland et al., but found that indoles having a free 3-position will react with phthalaldehydic acid under milder conditions. Indole and its 2-phenyl, 2-methyl, 7-methyl and 1,2-dimethyl derivatives were reported to react in hot benzene to yield the corresponding 3-phthalidyl indoles which results were attributed to intramolecular acid catalysis. In solution phthalaldehydic acid exists in the cyclic form, 3-hydroxyphthalide, which is in rapid equilibrium with the open-ring form, o-formylbenzoic acid. Presumably, the indole reacts with the aldehyde form and the carboxyl group ortho to the aldehyde group functions as an intramolecular acid catalyst. The authors observed that reactions with indole and 2-methyl indole also were catalyzed by an external acid catalyst, such as toluene-p-sulfonic acid, and also that a second mole of indole could be added to 3-phthalidylindole by opening the lactone ring with alkali and treating the resulting salt with a second mold of indole.

Rees et al. in further studies, ibid., pp. 687-91 (1965), reported that the condensation of phthalaldehydic acid could be extended to pyrroles and found that phthalaldehydic acid reacted with pyrrole and 2,5-dimethyl pyrrole in boiling benzene in the absence of an external catalyst to give high yields of 2-phthalidyl-pyrrole and 3-phthalidylpyrrole, respectively. In these reactions, it was observed that pyrrole tended to substitute in the 2-position when possible to yield the 2-phalidyl derivative. In a further extension of the reactions, the authors found that naphthalaldehydic acid, though less reactive than phthalaldehydic acid, behaved in a similar manner and could be condensed with indole under fusion conditions to yield 3-naphthalidylindole.

Aforementioned copending application Serial No. 108,662 provides a novel method of preparing phthalein indicator dyes which comprises reacting certain hydroxy-substituted carbocyclic compounds selected from a phenol and a 1-naphthol or certain N-heterocyclic aryl compounds selected from an indole and a pyrrole with phthalaldehydic or naphthalaldehydic acid to form the corresponding (na)phthalidyl-substituted intermediate, oxidizing the intermediate and reacting the oxidation product with an aromatic compound selected from carbocyclic aryl and heterocyclic aryl to form the complete indicator dye. As used herein, the expression "(na)phthalidyl" is intended to denote either the corresponding phthalidyl- or naphthalidyl-substituted intermediate depending upon the selection of phthalaldehydic or naphthalaldehydic acid.

Specifically, the method of the copending application comprises:

1. reacting a compound selected from a) a hydroxysubstituted carbocyclic aryl compound having a free position para to the hydroxy group selected from a phenol and a 1-naphthol and b) an N-heterocyclic aryl compound having hydrogen substituted on the nitrogen atom selected from an indole having a free 3-position and a pyrrole having a free 2-position with a compound selected from phthalaldehydic and naphthalaldehydic acid to form a compound having the formula:

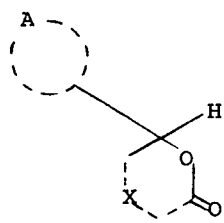

wherein A is selected from p-hydroxyphenyl, p-hydroxynaphthyl, indol-3-yl and pyrr-2-yl and X represents the carbon atoms necessary to complete a ring-closing moiety selected from phthalide and naphthalide;

2. converting the last-named compound by oxidation to a compound selected from

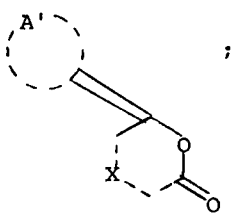

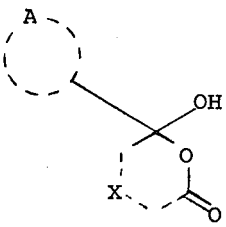 and mixtures thereof and mixtures thereof
wherein A' is selected from

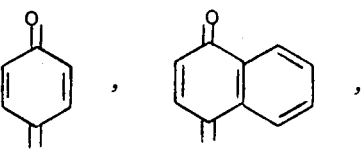

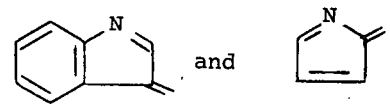

and A and X have the same meaning as above; and 3. reacting said last-named compound with an aromatic compound selected from a carbocyclic aryl compound and a heterocyclic aryl compound to form an indicator dye of the formula:

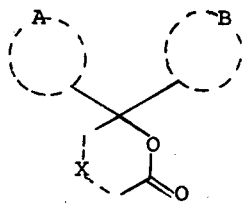

wherein B is selected from carbocyclic aryl and heterocyclic aryl and A and X have the same meaning as above.

The above reaction scheme is illustrated below wherein A'' represents the starting phenol, naphthol, indole or pyrrole which ultimately comprises the A radical of the indicator dye and B' represents the carbocyclic aryl or heterocyclic aryl compound which ultimately comprises the B radical of the indicator dye and X represents the carbon atoms necessary to complete the phthalide or naphthalide moiety.

1. 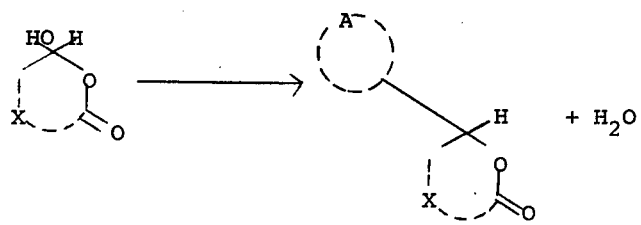

2. 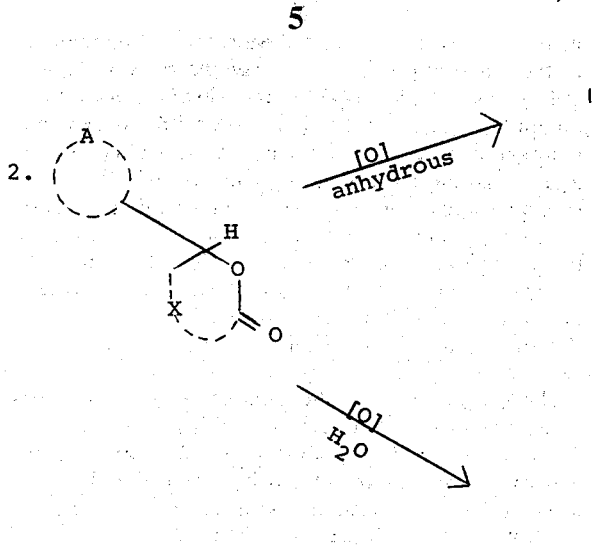

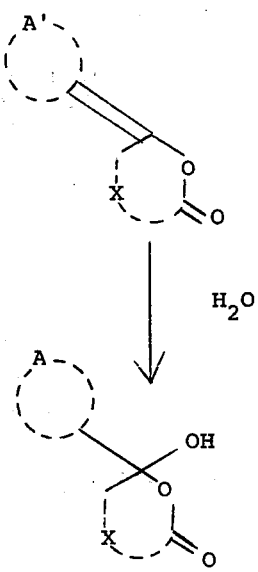

3. 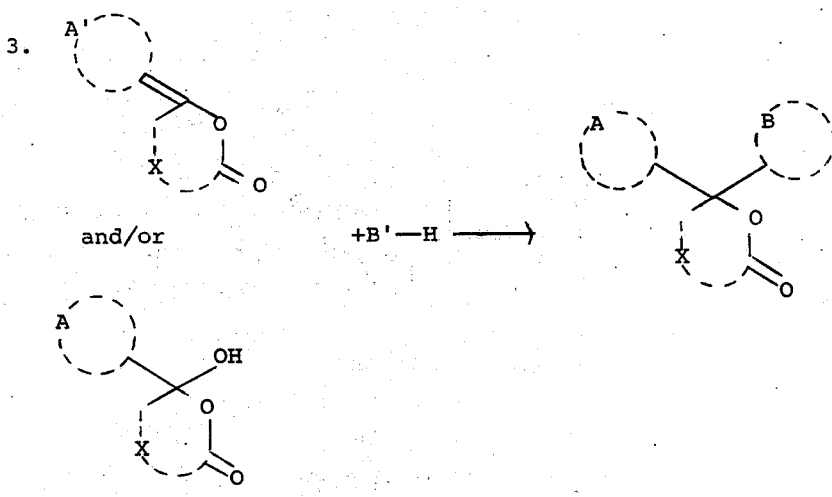

Since the reaction conditions are comparatively mild, this method allows greater latitude in the selection of starting materials. For example, the indole derivatives to be initially reacted with the acid are not limited to the more stable compounds but may include alkali and acid sensitive compounds as well. This method also allows greater latitude in the indicator dyes that may be produced. The dehydro and/or hydrated intermediates obtained in step 2 may be reacted with any of various aromatic compounds to form a complete dye so that both symmetrical and unsymmetrical phthalides and naphthalides and also, mixed indicator dyes, such as phthalides and naphthalides containing, for example, one phenol radical and one indole radical, may be readily synthesized.

The present invention is directed to another class of intermediates comprising protonated phthalides and naphthalides useful in the synthesis of phthalein and naphthalein indicator dyes.

SUMMARY OF THE INVENTION

It is, therefore the primary object of the present invention to provide novel protonated compounds useful as intermediates in the preparation of certain indicator dyes.

Other objects of this invention will in part be obvious and will in part appear hereinafter.

The invention accordingly comprises the product possessing the features, properties and the relation of elements which are exemplified in the following detailed disclosure and the scope of the application of which will be indicated in the claims.

For a fuller understanding of the nature and objects of the present invention reference should be had to the followed detailed description.

DESCRIPTION OF THE PREFERRED EMBODIMENTS

Specifically, the present invention provides certain protonated compounds which may be represented by the formula:

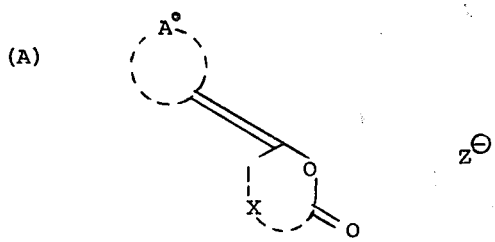

wherein A is a radical, substituted or unsubstituted, selected from acid is the hydrated form, the water should be removed as the reaction proceeds, for example, by distillation.

The protonated compound thus obtained is useful as an intermediate for condensation with an aromatic compound selected from a carbocyclic aryl compound and a heterocyclic aryl compound to form the corresponding indicator dye. The condensation reaction may be conducted by refluxing the protonated compound and selected aromatic compound in any inert organic solvent at room temperature or elevated temperature, usually between about 20°C. and 120°C., and, if desired, may be carried out in the presence of an acid catalyst.

The preparation of the subject protonated compounds from the hydrated form, as exemplified by 3-hydroxy-3-(4'-hydroxyphenyl)phthalide and from the dehydro form, as exemplified by 3-(indol-3-yl) dehydronaphthalide, by reaction with a protic acid, HZ, is illustrated in the following reaction schemes.

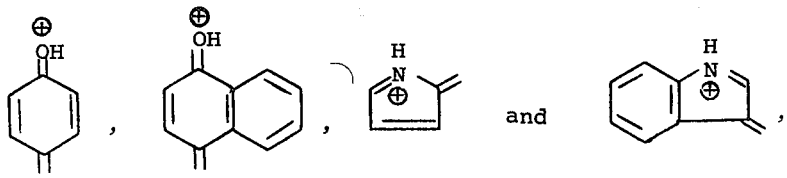

(i)

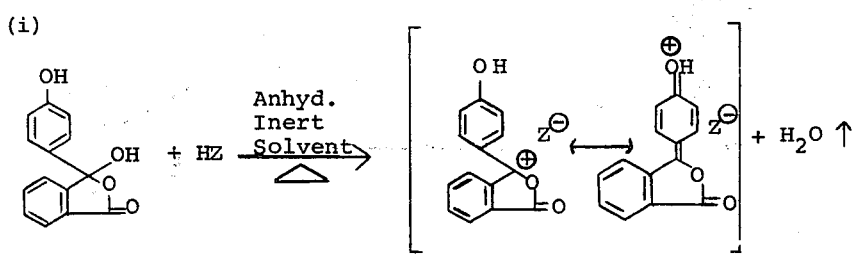

(ii)

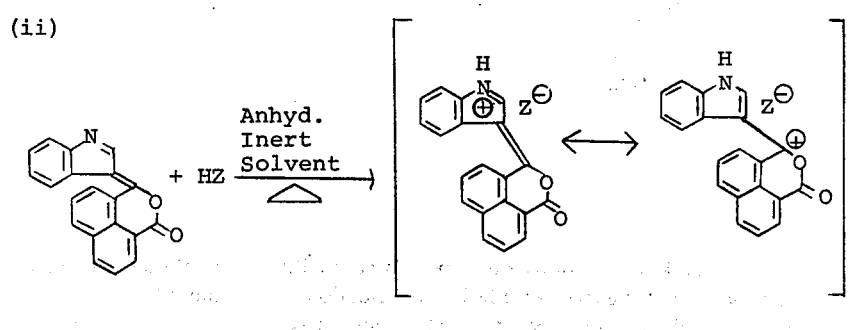

X represents the atoms necessary to complete a ring-closing moiety selected from phthalide and naphthalide, and Z is an anion derived from a protic acid having a pKa less than 4.0, for example, an inorganic acid, such as, sulfuric acid or an organic acid, such as, toluene-para-sulfonic acid.

These protonated compounds may be prepared by reacting the dehydro and/or hydrated product of step 2 of aforementioned application Ser. No. 108,662 with the selected protic acid under anhydrous conditions. Ordinarily, the dehydro and/or hydrated compound and the acid are reacted in an inert, anhydrous organic solvent at elevated temperature, usually between about 50° and 200°C. Where the compound reacted with the Rather than converting the dehydro and/or hydrated compounds of step 2 to the protonated compounds prior to the condensation step 3, the protonated compounds may be generated in situ during the condensation reaction. This is achieved by using a protic acid, such as, toluene-para-sulfonic acid as the acid catalyst in the condensation reaction. By proceeding in this manner, the indicator dyes may be prepared without the additional separate step of forming the protonated compound before condensing it with the selected aromatic compound to yield the dye. In this embodiment, the oxidation of step 2 preferably is conducted under anhydrous conditions to yield the dehydro(na)phthalide which, in the subsequent condensation step, is converted to the corresponding protonated (na)phthalide as shown in the following reaction sequence wherein TSOH and HOAc represent p-toluene sulfonic acid and acetic acid, respectively.

1a. 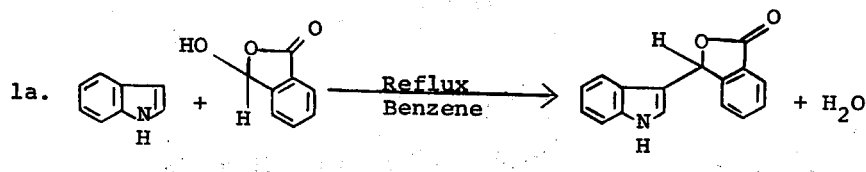

2a. 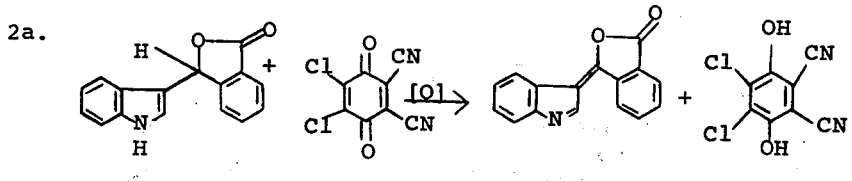

3a. 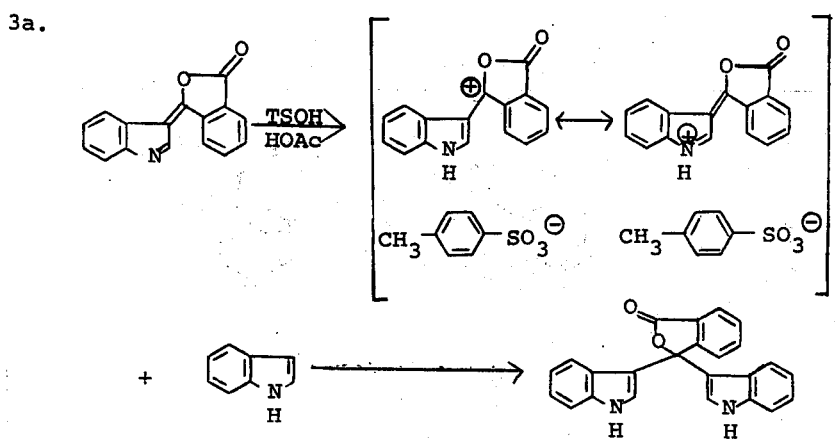

The subject protonated compounds have various resonance forms, the two principle resonance forms being those shown in the above reaction schemes. It is intended that the compounds of the present invention include the equivalent resonance forms of the structure as set out in formula (A).

Typical of the indicator dyes that may be prepared employing the protonated compounds of the present invention are those represented by the following formula:

(I) 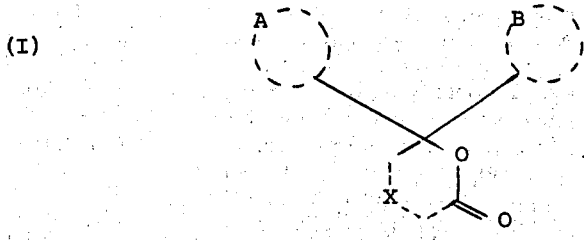

wherein A is a radical selected from p-hydroxyphenyl, p-hydroxynaphthyl, indol-3-yl and pyrr-2-yl, the N atoms of said indolyl and pyrryl radicals being substituted with hydrogen; B is a radical selected from carbocyclic aryl and heterocyclic aryl; and X represents the carbon atoms necessary to complete a ring-closing moiety selected from phthalide and naphthalide.

In the above formula, the B radical may be carbocyclic aryl of the benzene or naphthalene series, preferably benzene or naphthalene containing a para substituent, such as hydroxy, or it may be heterocyclic aryl containing O, N, S, P and combinations thereof, preferably N-heterocyclic aryl, such as indole, pyrrole or carbazole.

The A radical of the subject protonated compounds and the A and/or B radical and/or the ring-closing moiety of the indicator dyes represented above may contain one or more substituents in addition to those specified as may be readily selected by those skilled in the art to achieve certain desired properties.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as, phenyl, 2-hydroxyphenyl, 2-hydroxy-4-dodecyloxyphenyl, and naphthyl; alkaryl, such as, benzyl phenethyl, phenylhexyl, p-octylphenyl, p-dodecylphenyl; alkoxy, such as, methoxy, ethoxy, butoxy, 1-ethoxy-2-(β-ethoxyethoxy), dodecyloxy and octadecyloxy; aryloxy, such as phenoxy, benzyloxy, naphthoxy; alkoxyalkyl, such as methoxyethyl, dodecyloxyethyl; halo such as, fluoro, bromo, and chloro; trifluoroalkyl, such as, trifluoromethyl, mono- and bis-trifluoromethyl carbinol; sulfonamido (—NH—SO$_2$—R wherein R may be alkyl, aryl, alkaryl); sulfamoyl (—SO$_2$—NH—R wherein R may be alkyl, aryl, alkaryl); acyl and its derivatives

wherein R' may be hydrogen, alkyl, aryl, alkaryl); aminomethyl (—CH$_2$—NR'R'' wherein R' and R'' each may be hydrogen, alkyl, aryl, alkaryl); amido

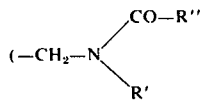

wherein R' and R'' each may be hydrogen, alkyl, aryl, alkaryl); sulfonyl (—SO$_2$—R wherein R may be alkyl, aryl, alkaryl); sulfo; cyano; nitro; amino including mono- and disubstituted amino, e.g., N-ethyl amino and N, N'-dimethylamino; carboxy; and hydroxyl.

In addition to the above, the substituent may comprise a fused ring bonded to adjacent atoms of the aromatic nucleus. For example, the indoles, pyrroles, phenols and 1-naphthols comprising one or both of the A and B radicals may contain as a substituent a cycloaliphatic or an aromatic ring usually having 5 or 6 members, carbocyclic or heterocyclic and substituted or unsubstituted, bonded to adjacent carbon atoms of the basic compound, e.g.,

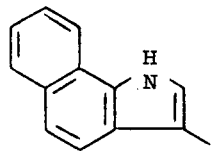 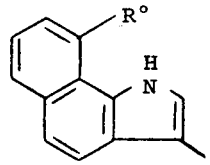

wherein R° is, e.g., -OH or -COOH

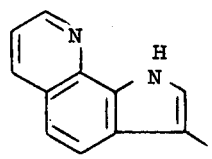 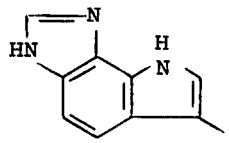 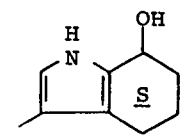

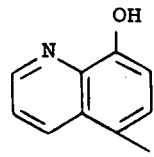 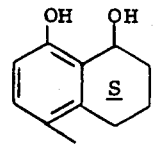 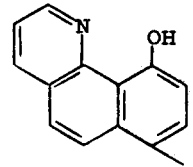

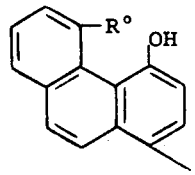

wherein R° is, e.g., -OH or -COOH.

wherein R is, e.g., —OH or —COOH.

As mentioned previously, the indicator dyes produced in accordance with the present invention may be symmetrical, i.e., di-phthalides or di-naphthalides in which instance the B radical would be identical to the A radical, or they may be unsymmetrical or mixed indicators. When unsymmetrical, the A radical and B radical would be derived from the same aromatic compound such as, indole, but each radical would contain different substituents or the same substituents in different positions or one radical would be substituted and the other unsubstituted. The term "mixed indicator" is intended to denote indicator dyes where the A radical and B radical are derived from different aromatic compounds, for example, one from indole and the other from phenol.

Examples of specific indicator dyes that may be prepared according to the present invention include:

(1) 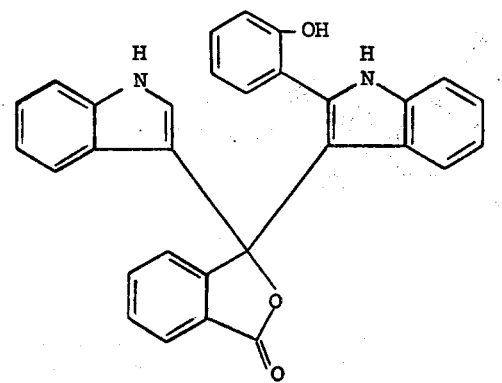
(2) 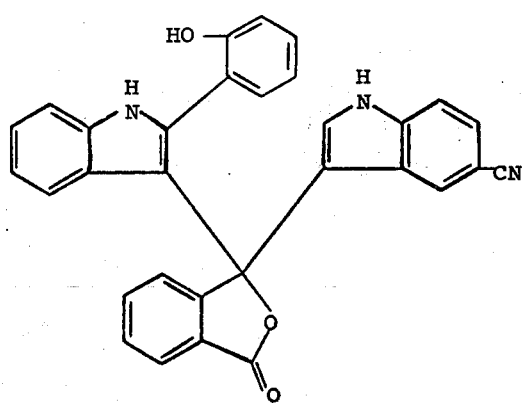
(3) 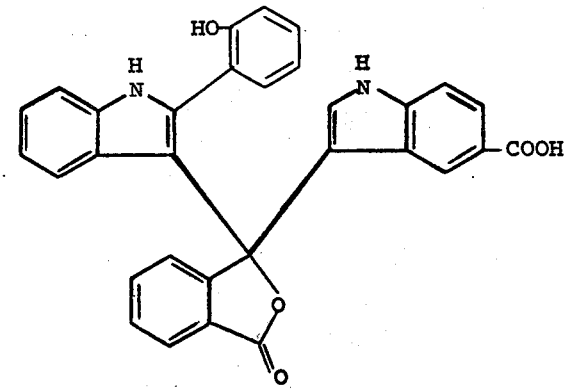
(4) 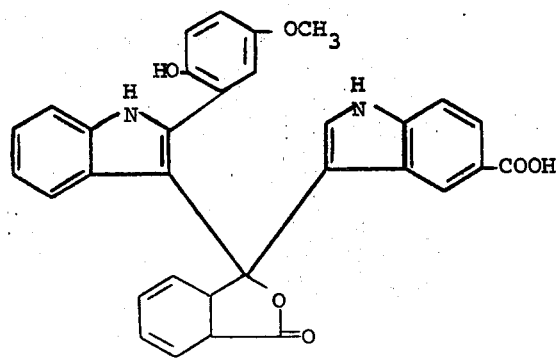

(5) 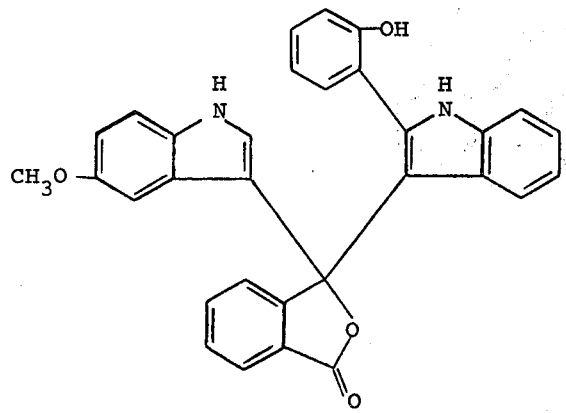
(6) 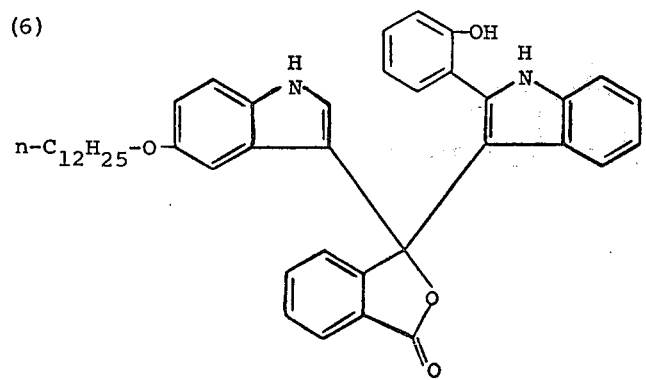
(7) 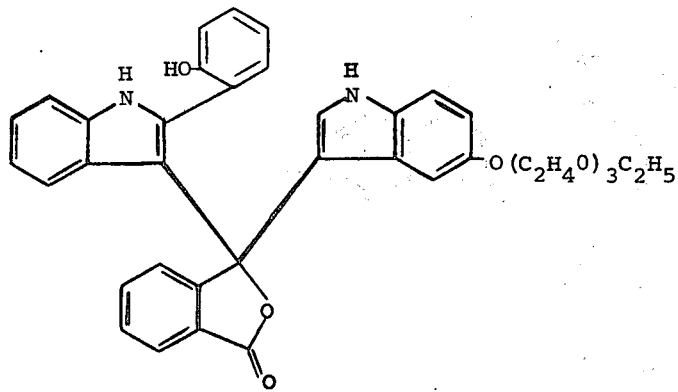
(8) 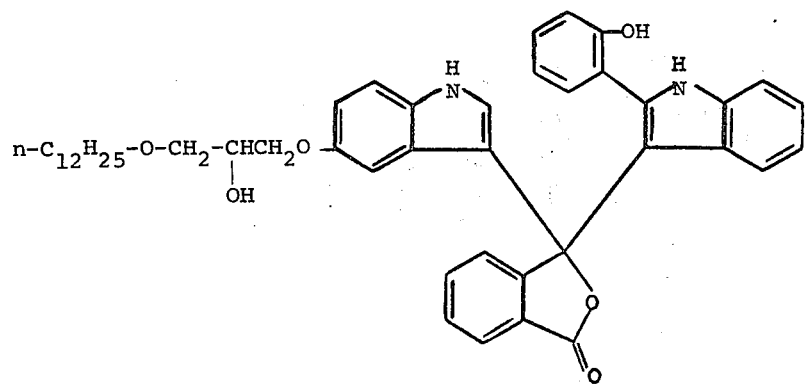

(9) 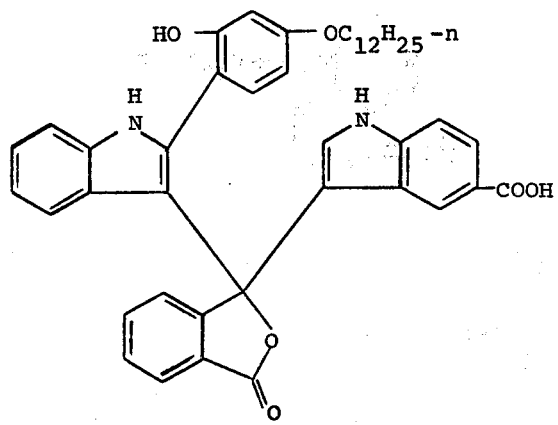
(10) 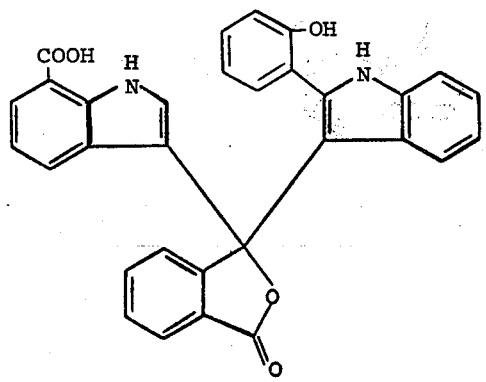
(11) 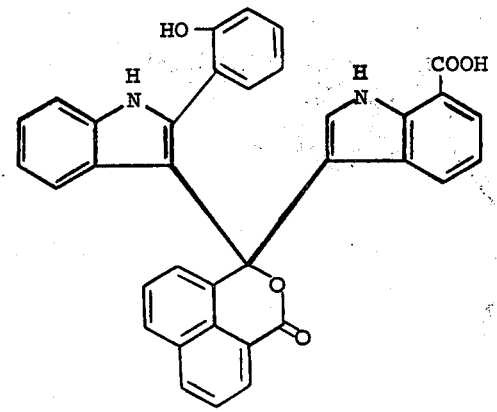
(12) 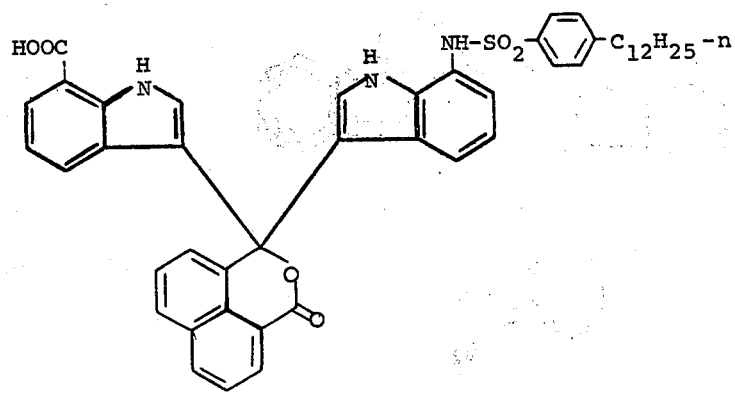

(13)
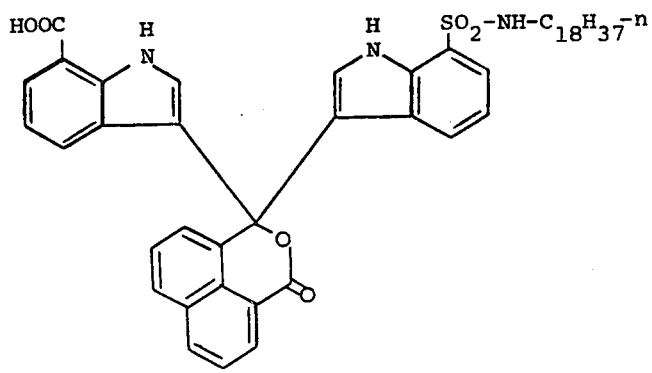
(14)
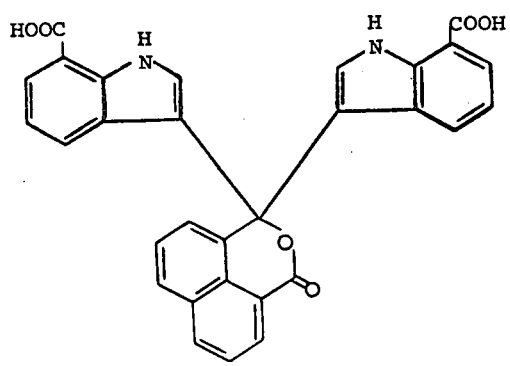
(15)
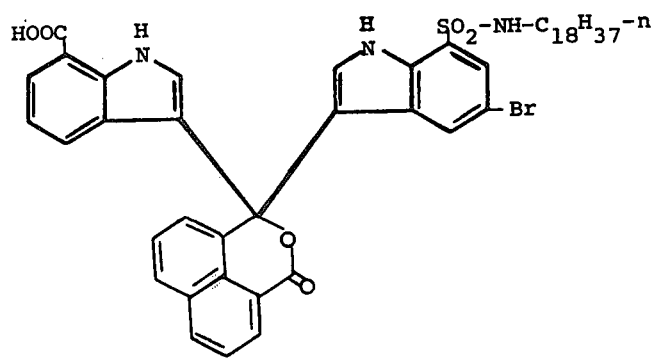
(16)
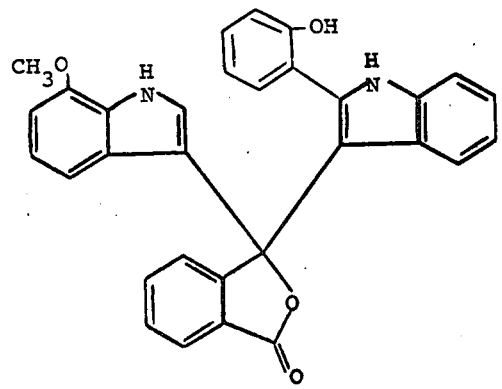

(17) 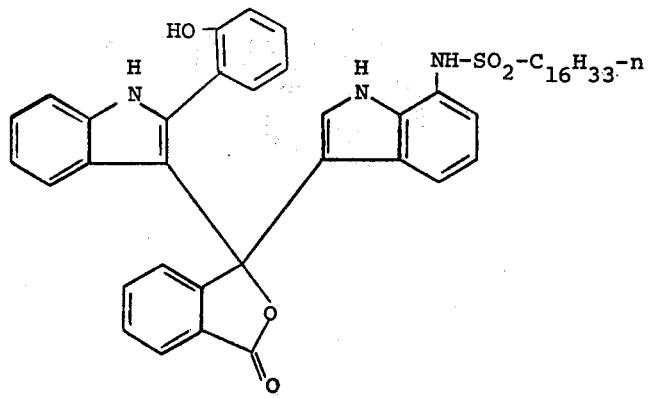
(18) 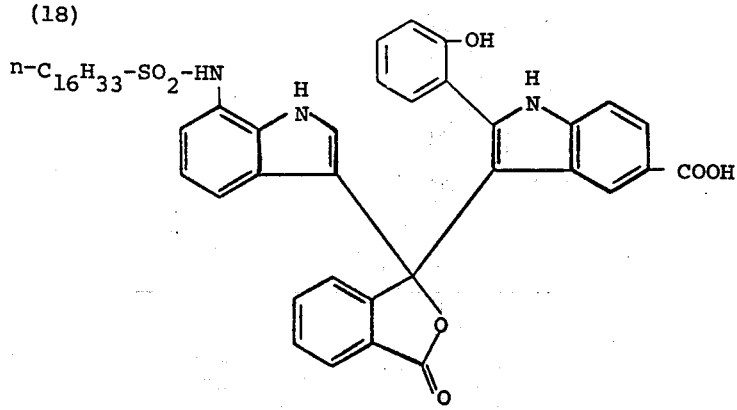
(19) 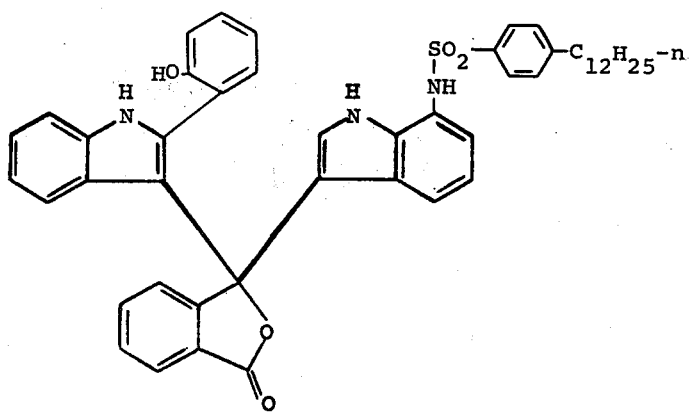
(20) 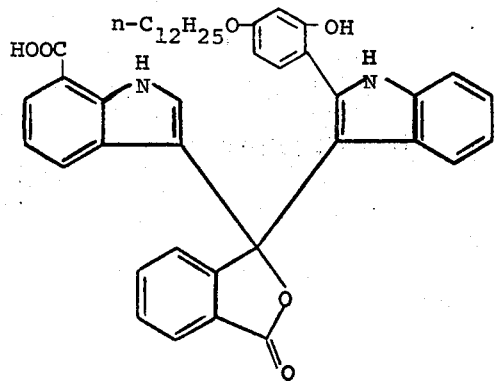

(21)
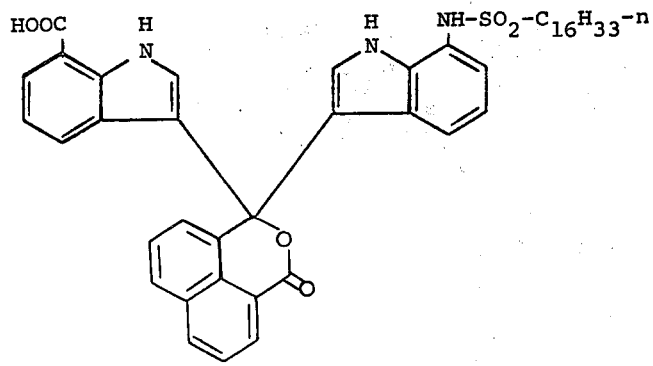
(22)
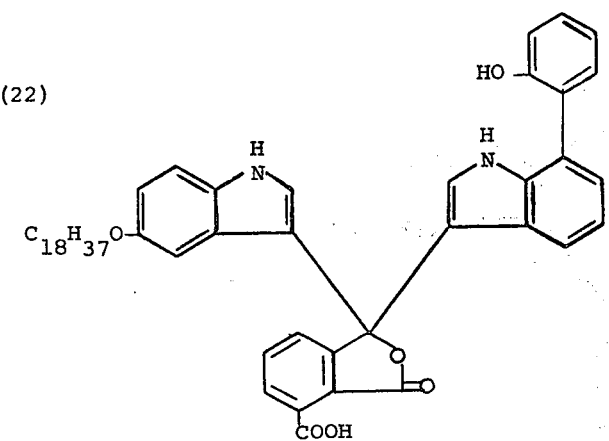
(23)
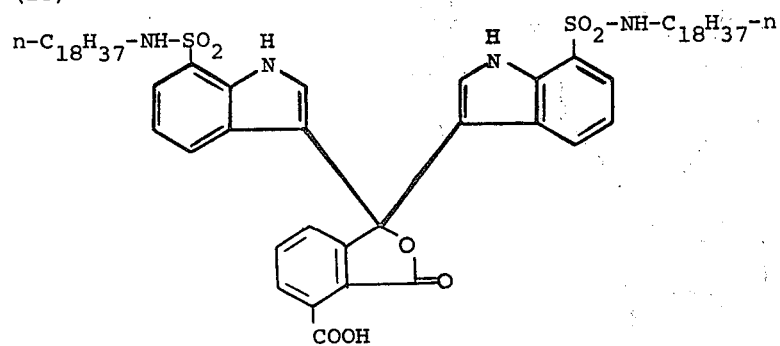
(24)
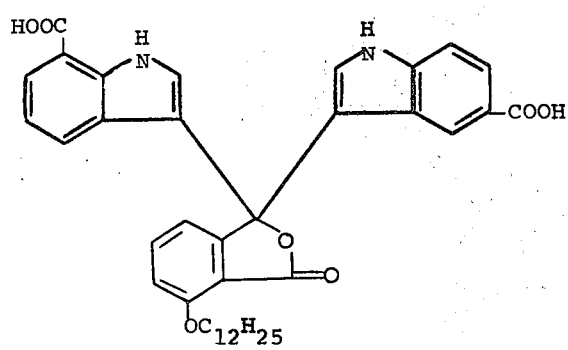

(25)
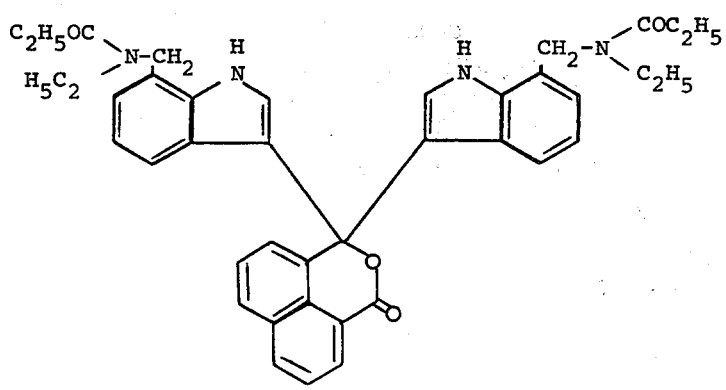
(26)
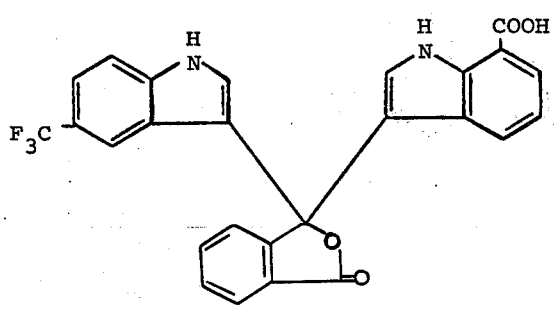
(27)
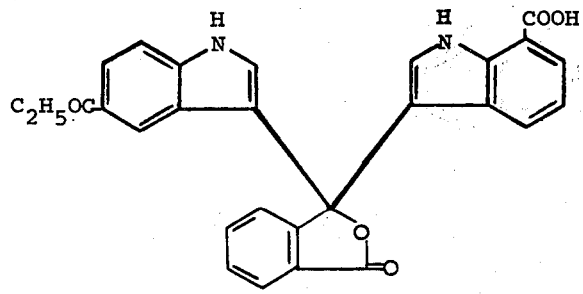
(28)
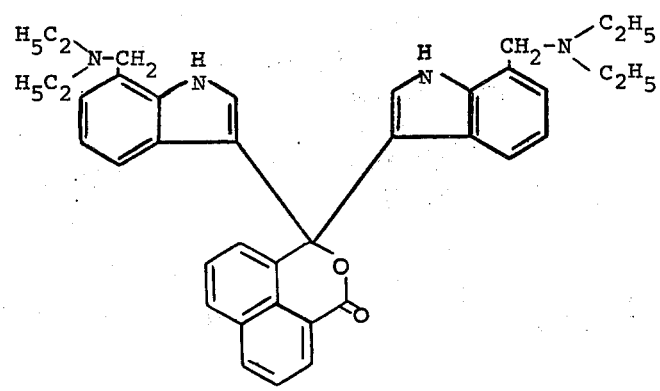

(29)
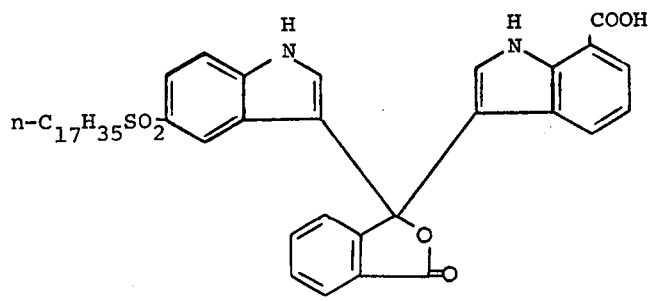
(30)
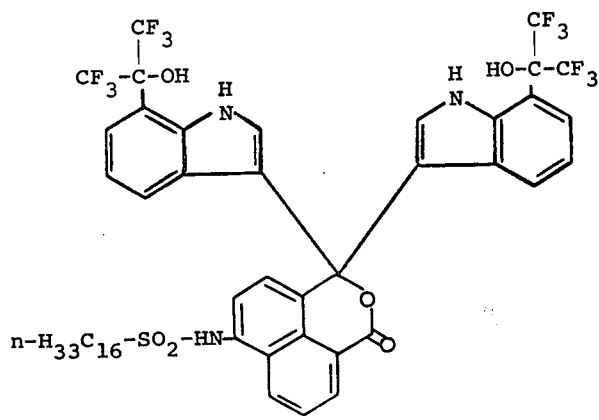
(31)
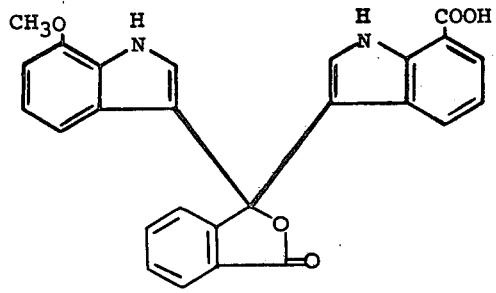
(32)
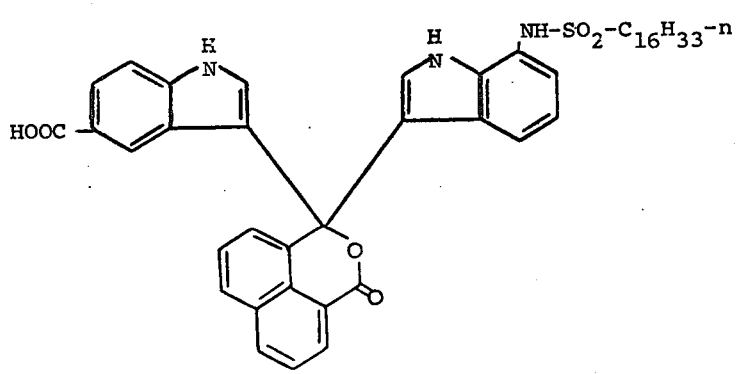

(33)
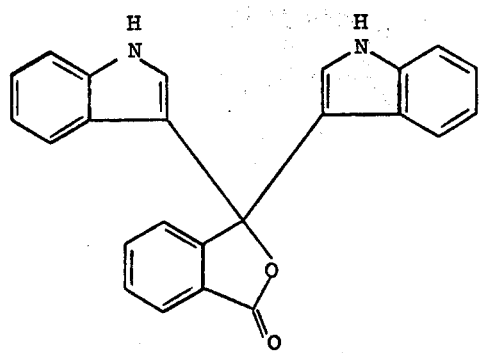
(34)
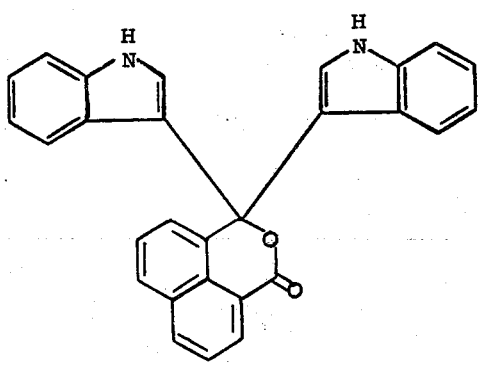
(35)
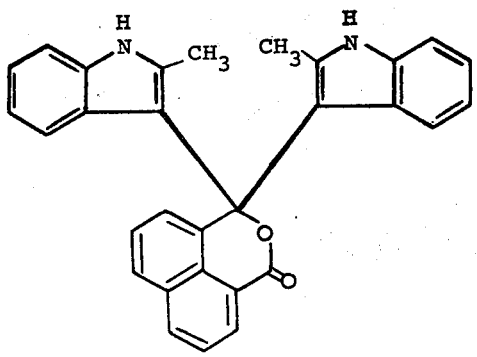
(36)
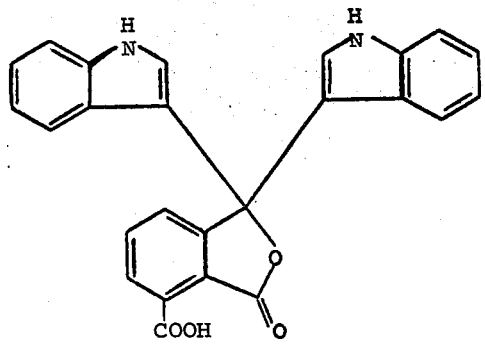

(37) 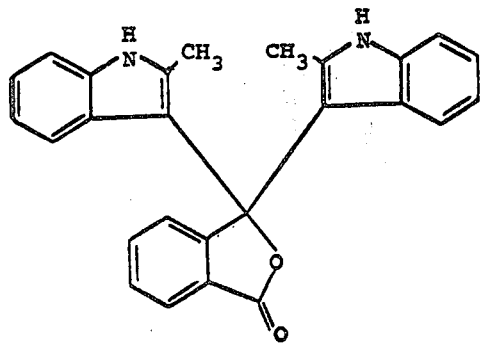
(38) 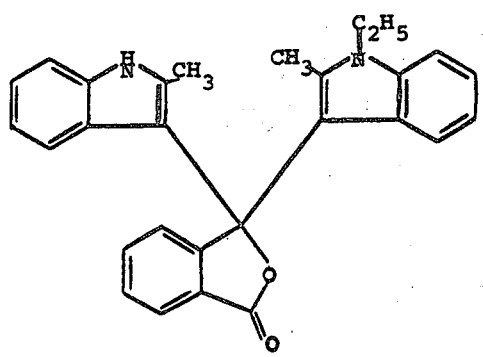
(39) 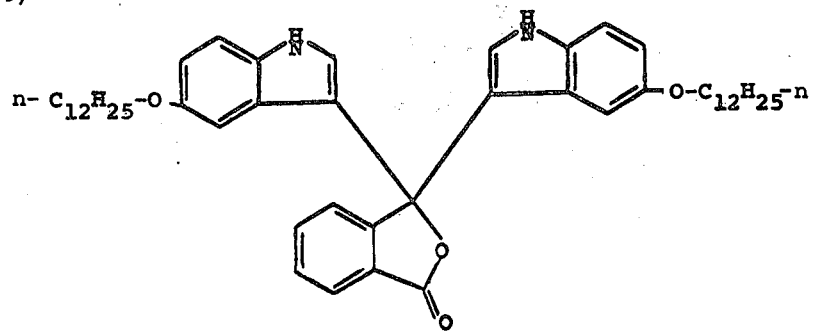
(40) 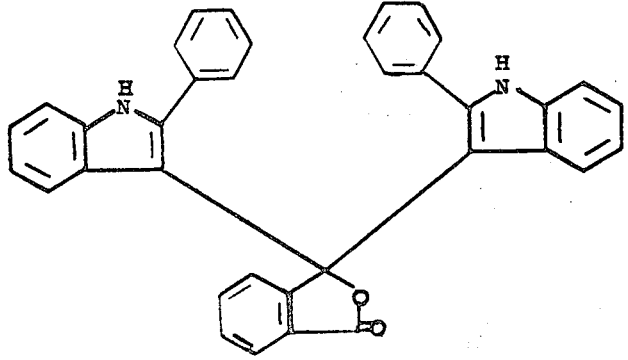

(41)
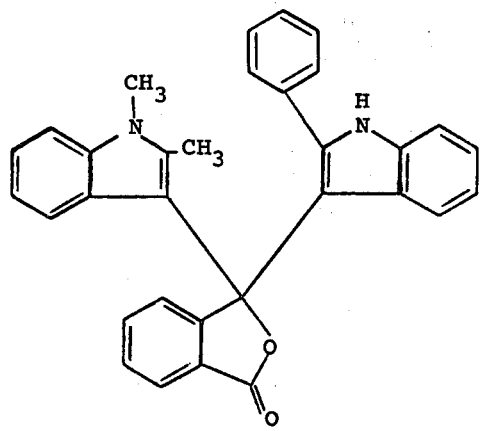
(42)
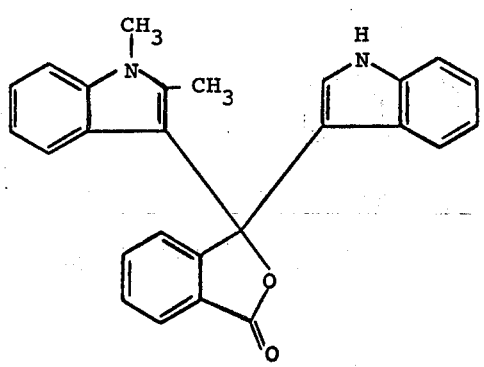
(43)
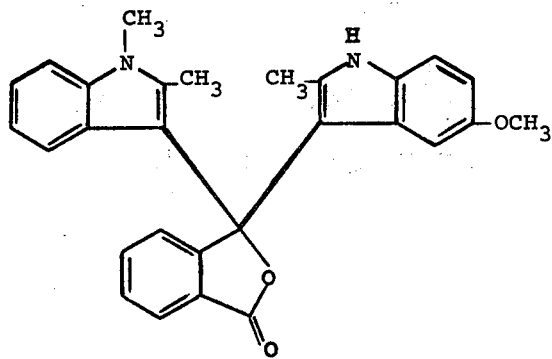
(44)
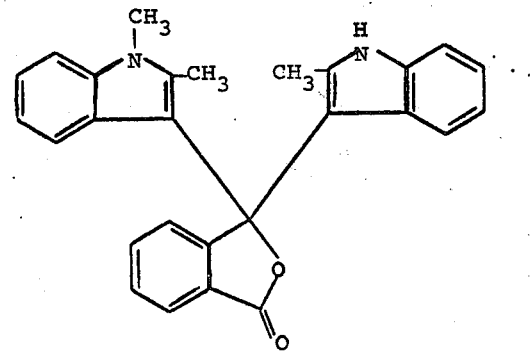

(45)
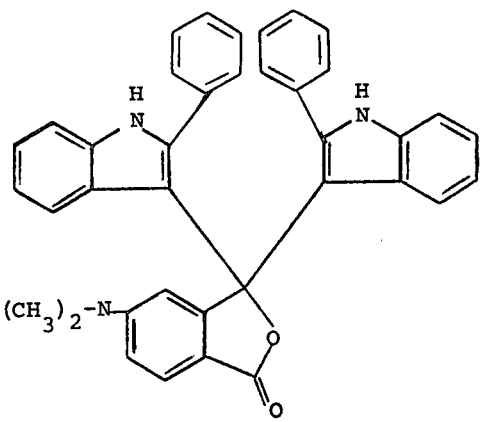
(46)
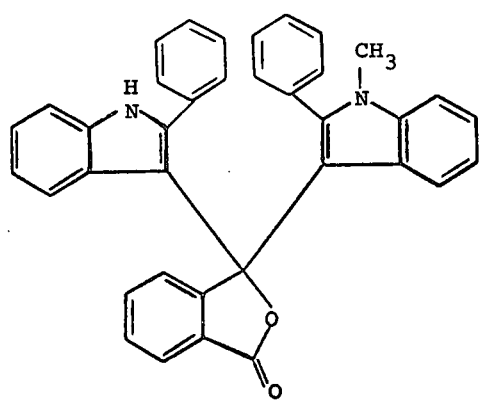
(47)
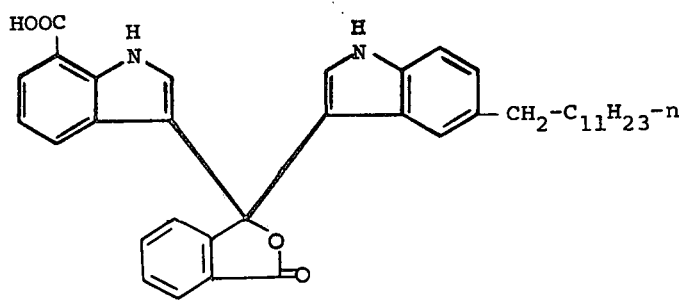
(48)
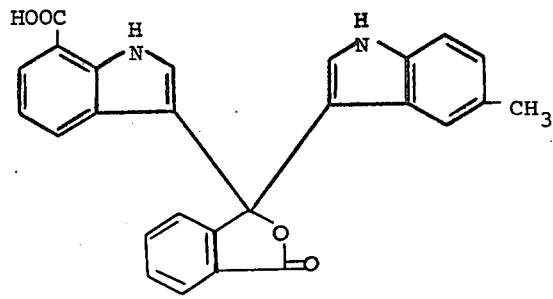

(49) 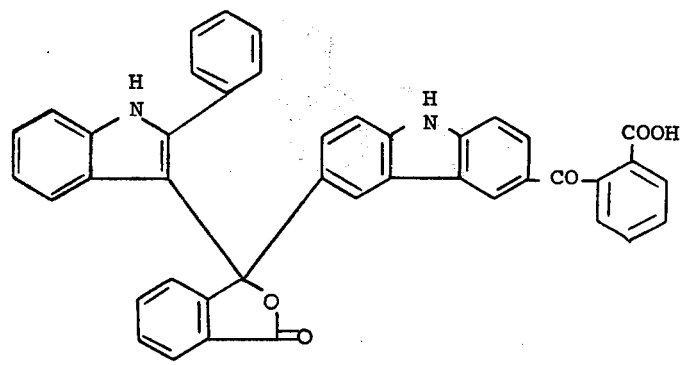
(50) 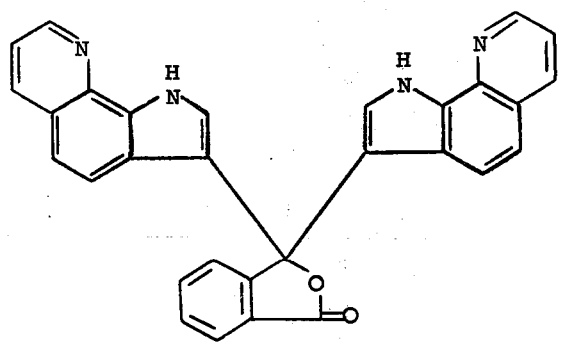
(51) 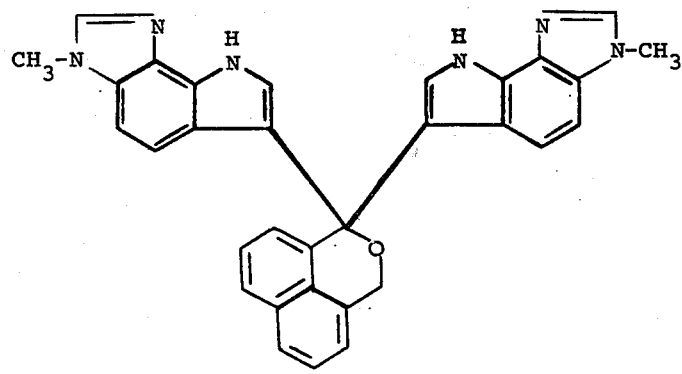
(52) 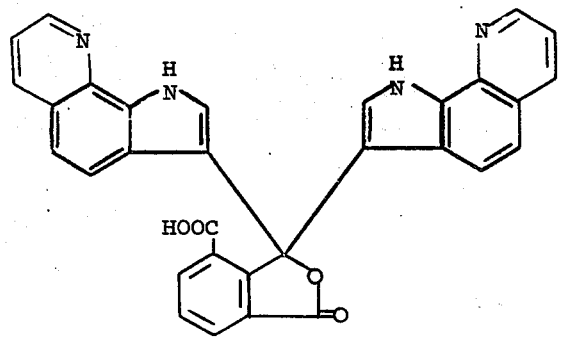

(53) 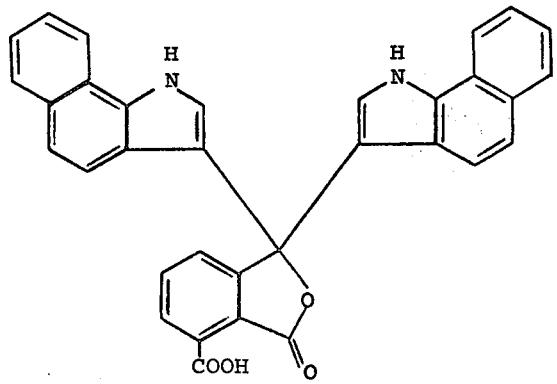
(54) 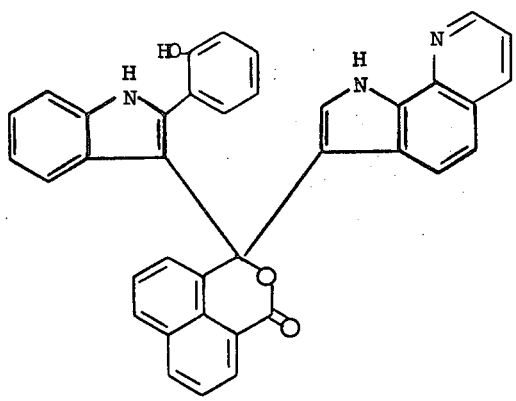
(55) 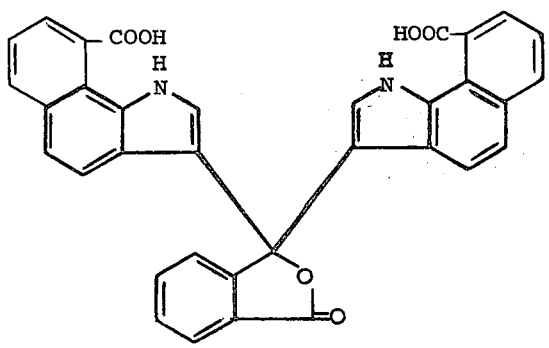
(56) 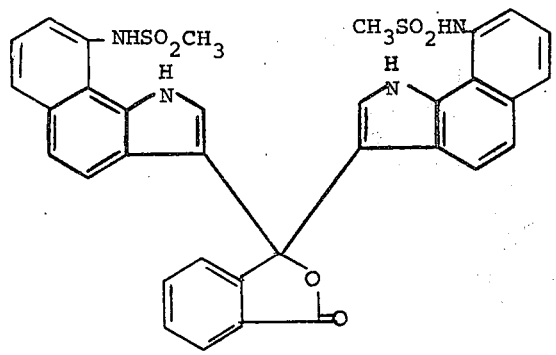

(57)
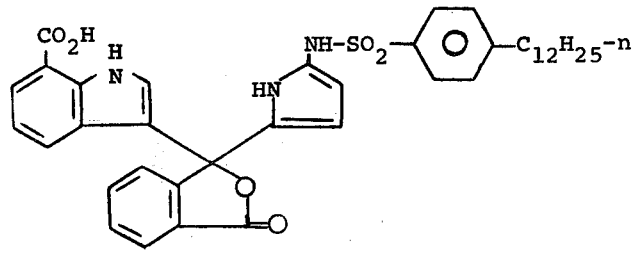
(58)
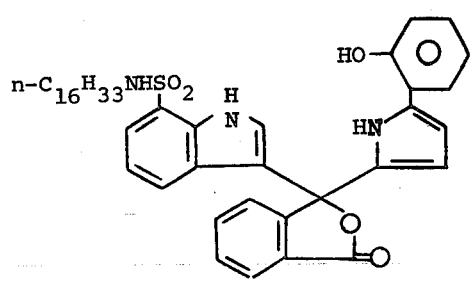
(59)
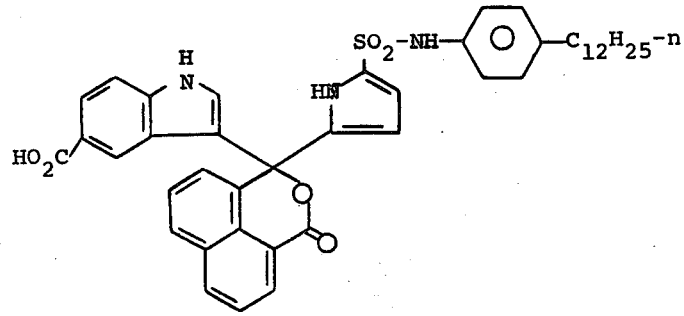
(60)
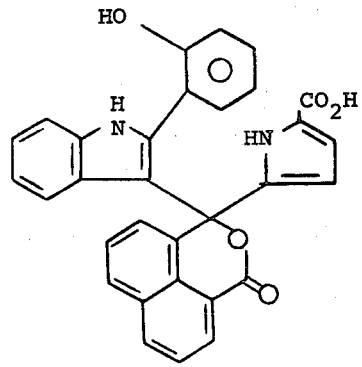

(61)
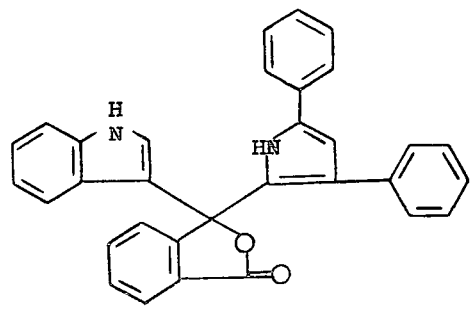
(62)
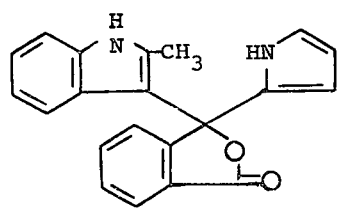
(63)
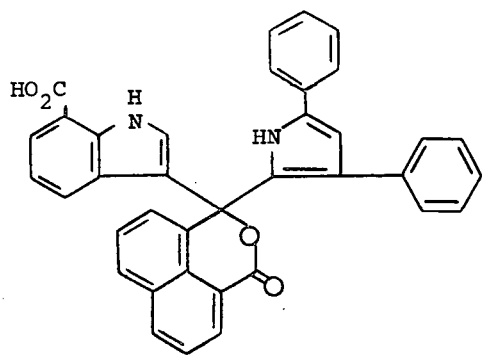
(64)
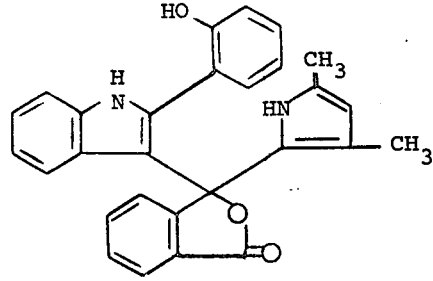
(65)
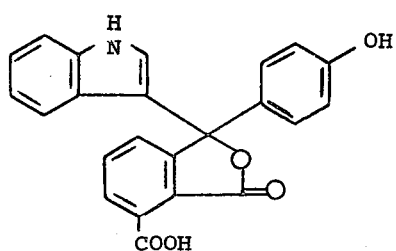

(66) 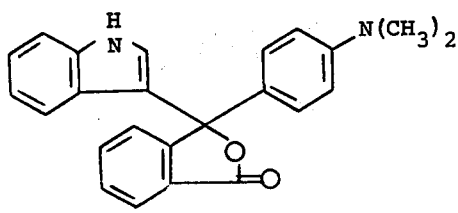
(67) 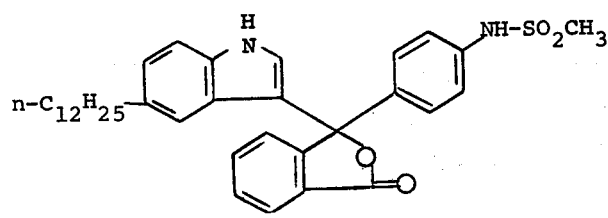
(68) 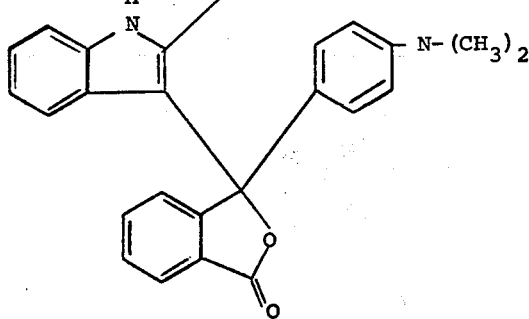
(69) 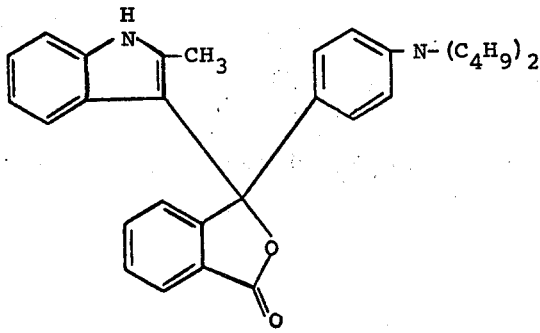
(70) 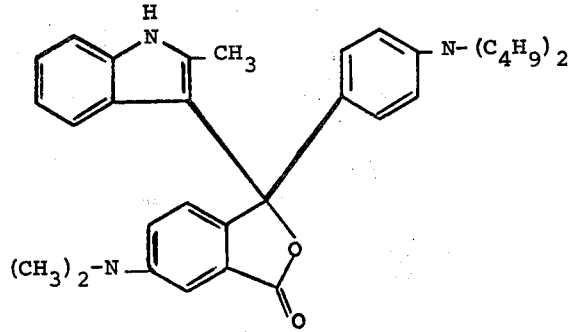

(71) 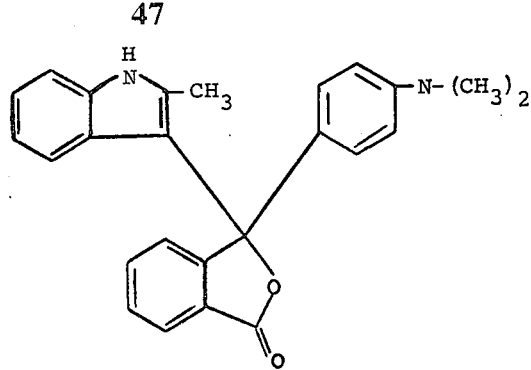
(72) 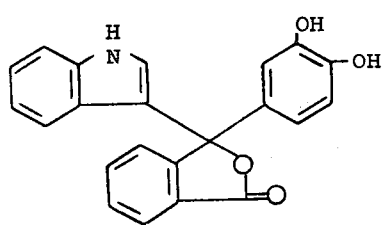
(73) 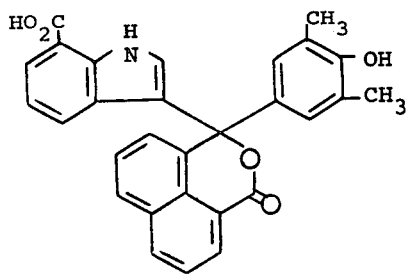
(74) 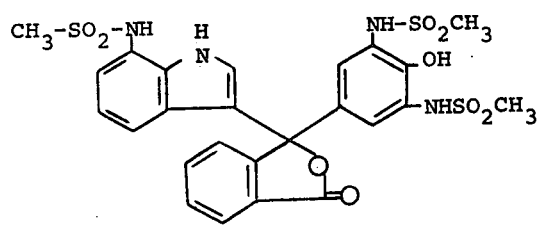
(75) 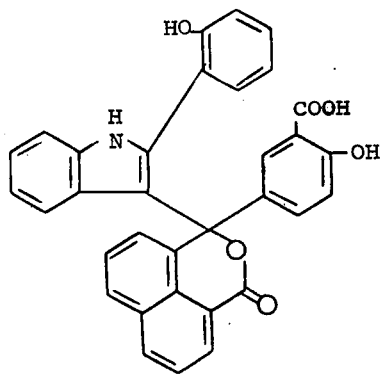

(76) 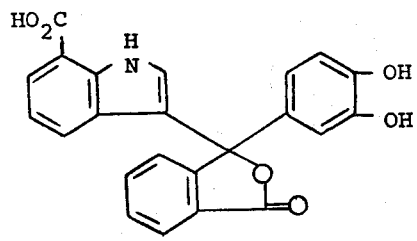
(77) 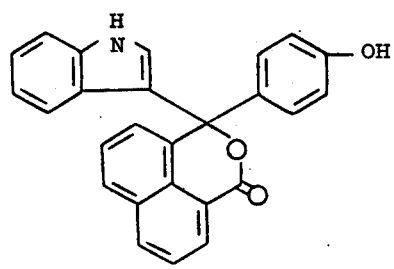
(78) 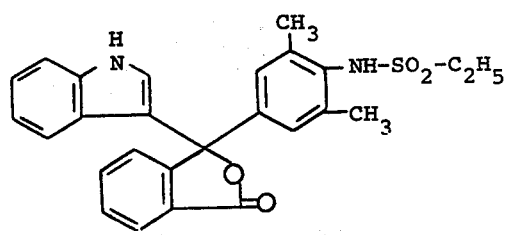
(79) 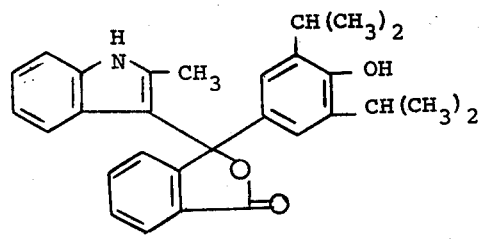
(80) 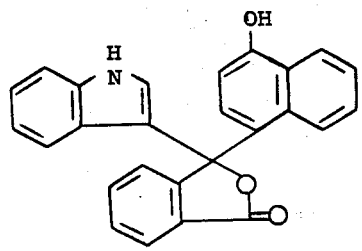

(81) 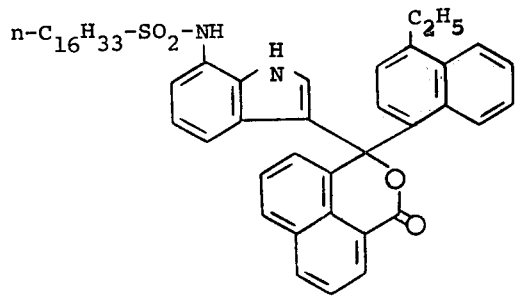
(82) 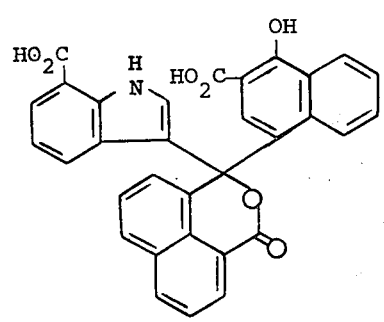
(83) 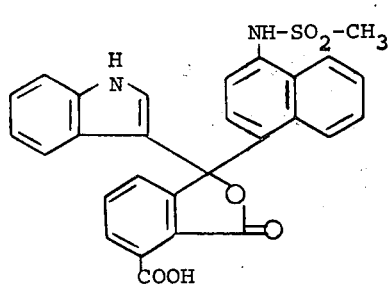
(84) 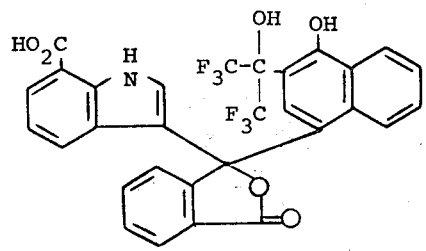
(85) 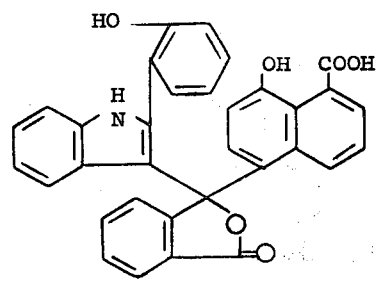

(86)
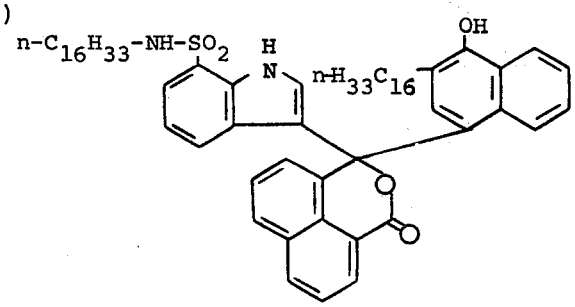
(87)
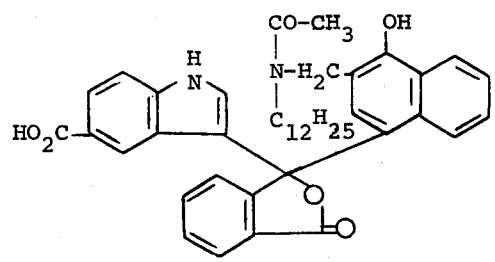
(88)
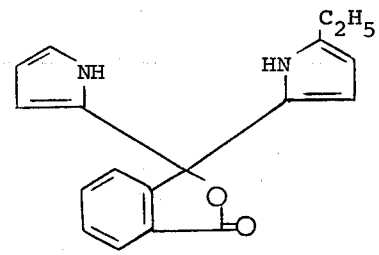
(89)
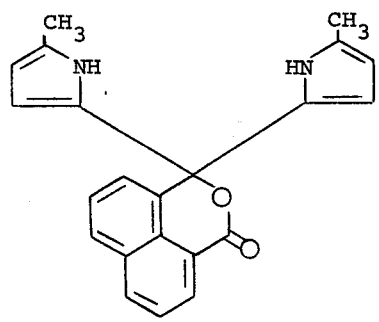
(90)
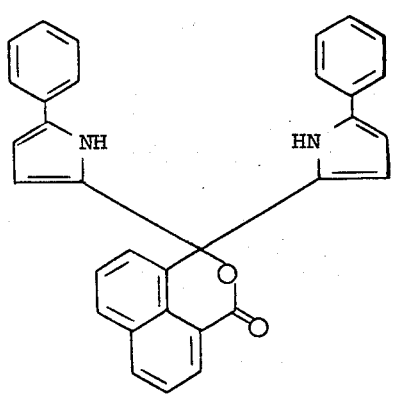

(91) 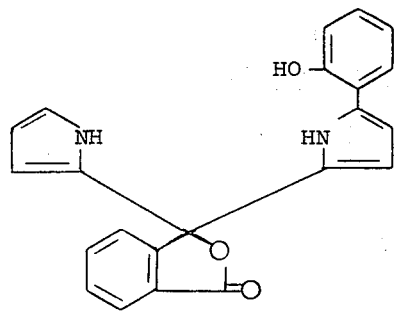
(92) 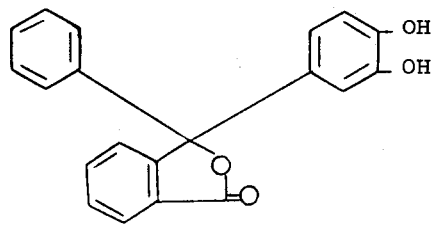
(93) 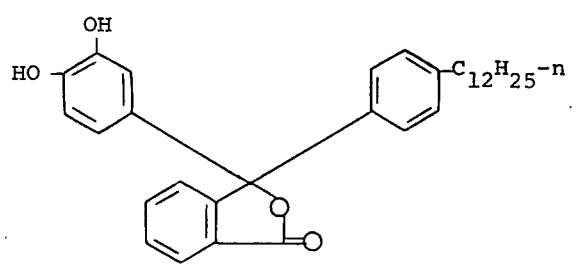
(94) 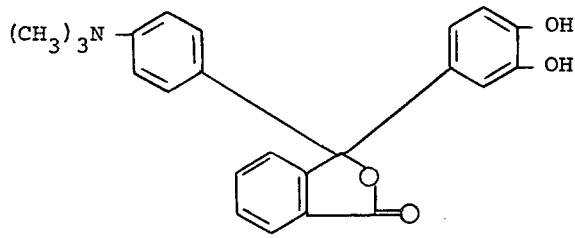
(95) 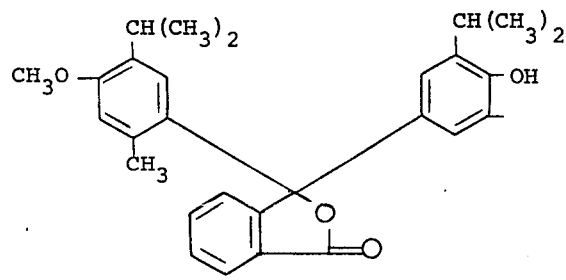

(96)
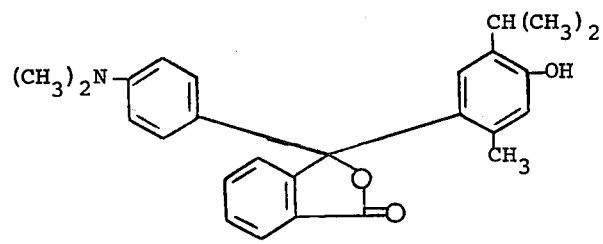
(97)
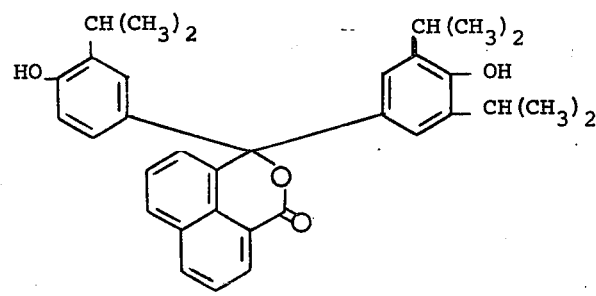
(98)
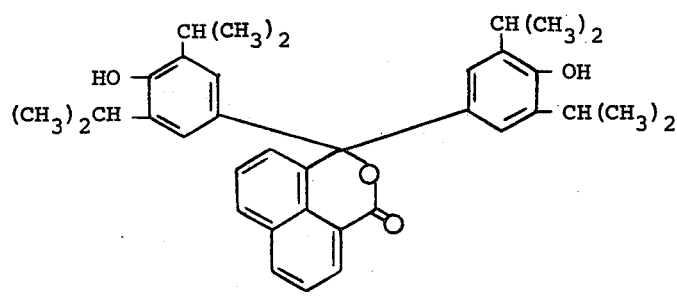
(99)
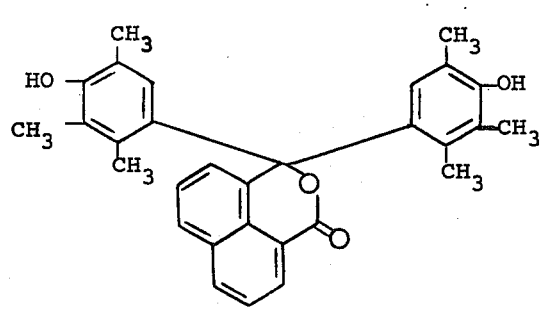
(100)
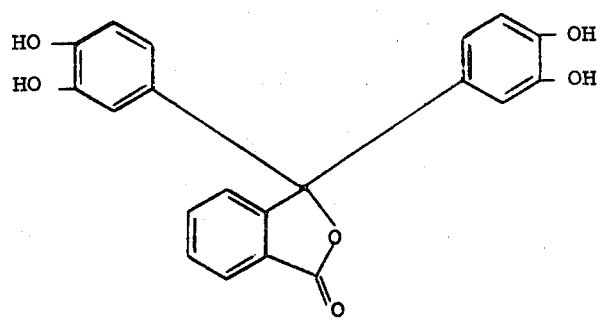

(101)
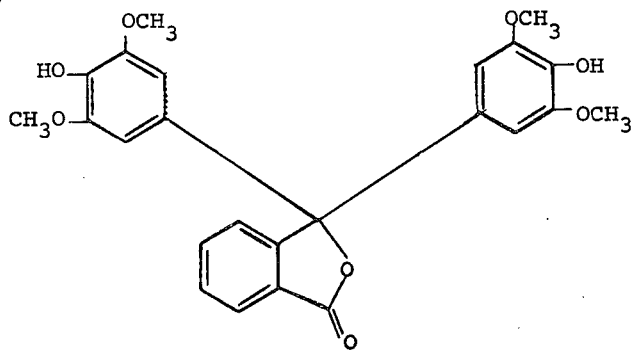
(102)
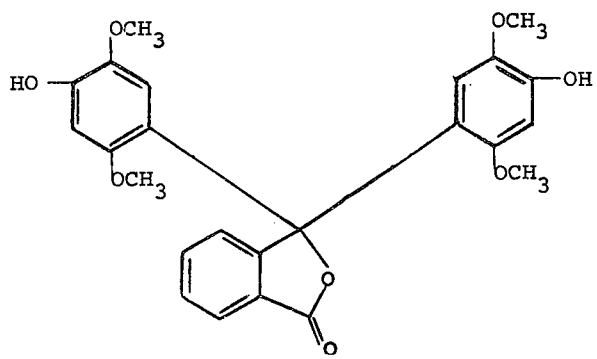
(103)
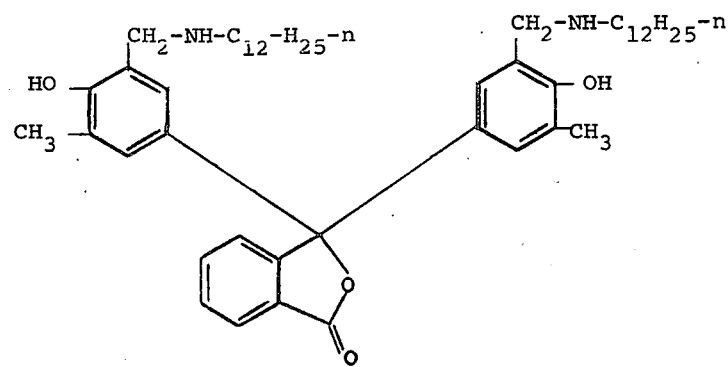
(104)
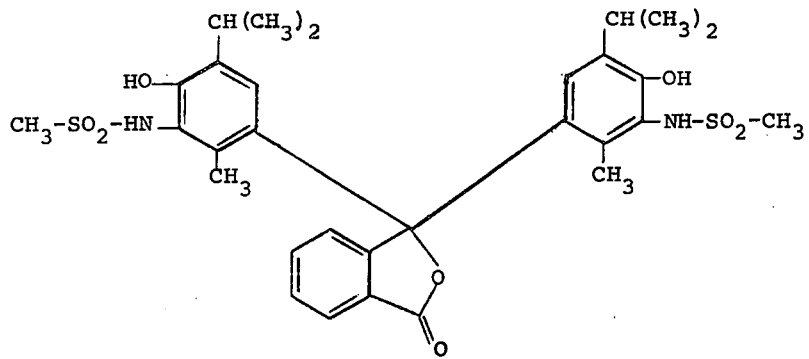

(105)
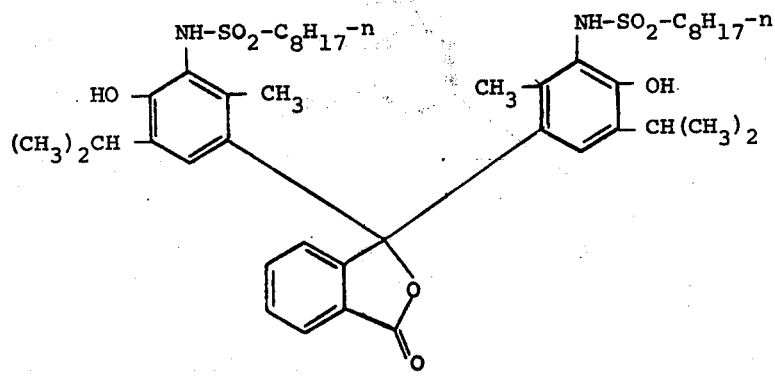
(106)
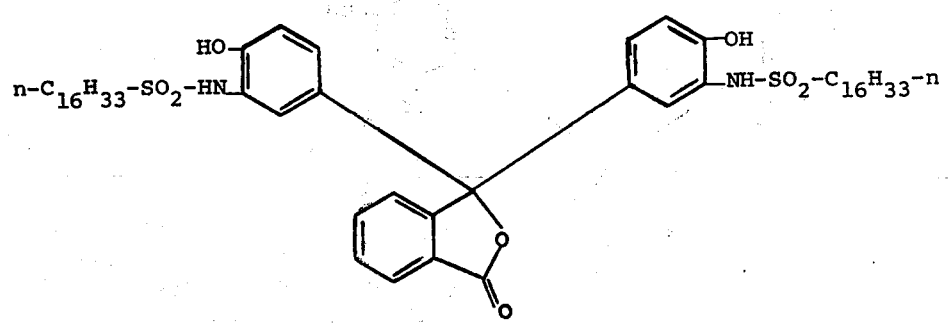
(107)
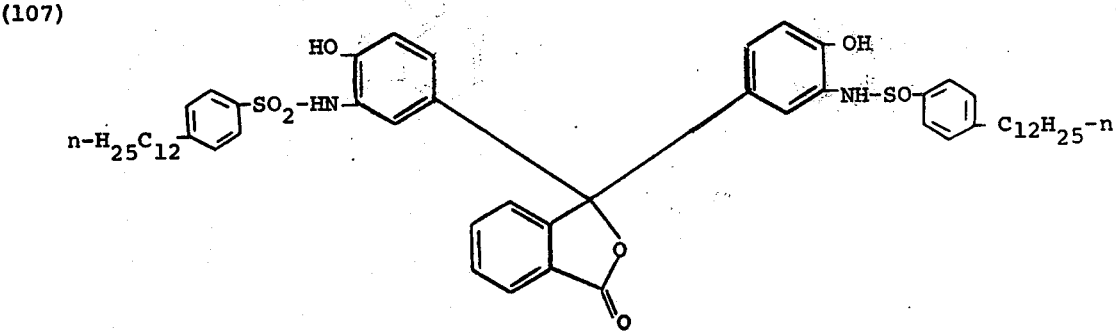
(108)
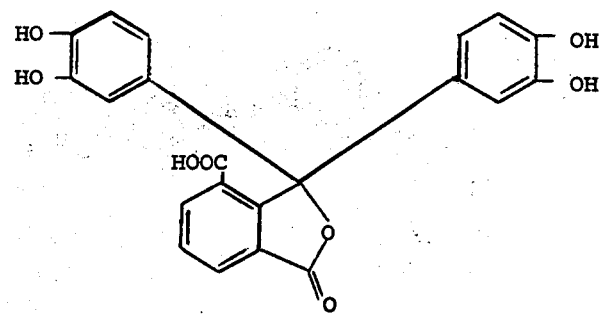

(109)
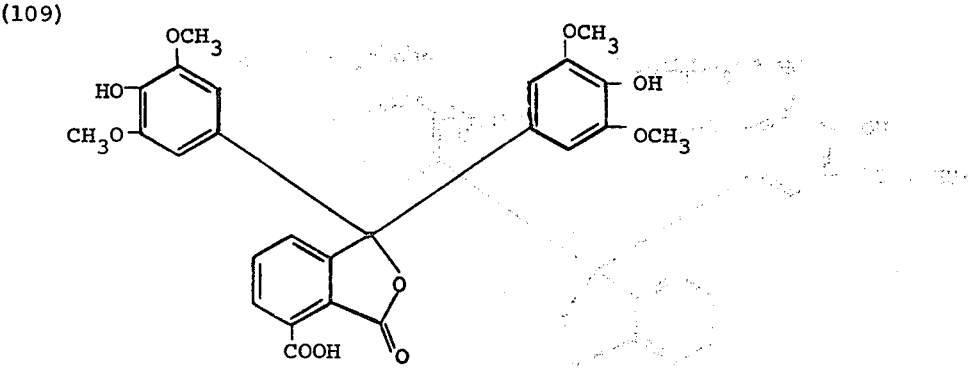
(110)
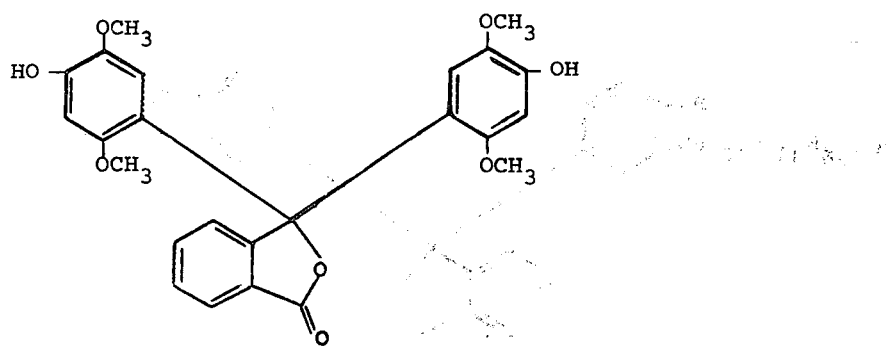
(111)
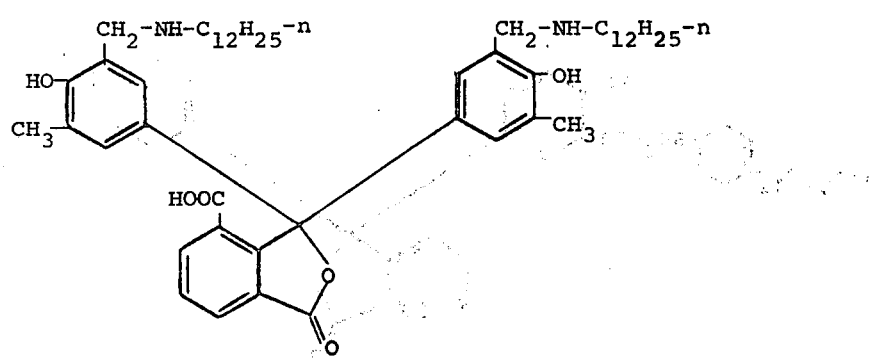
(112)
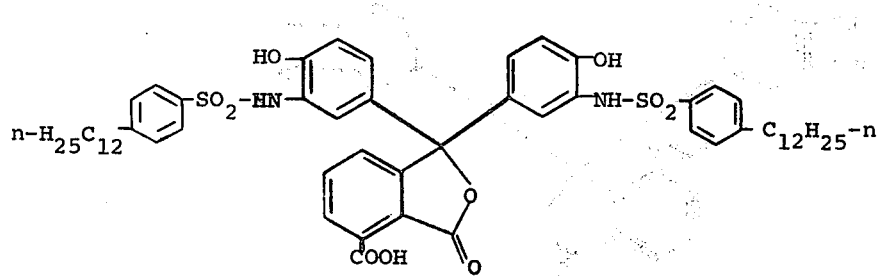

(113)
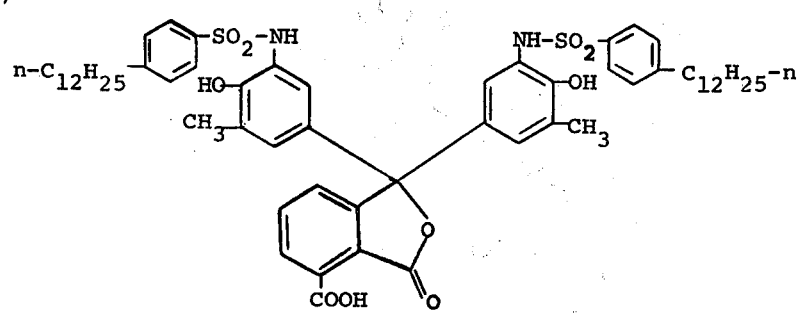
(114)
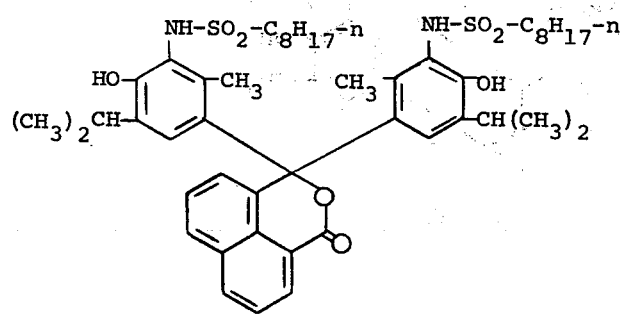
(115)
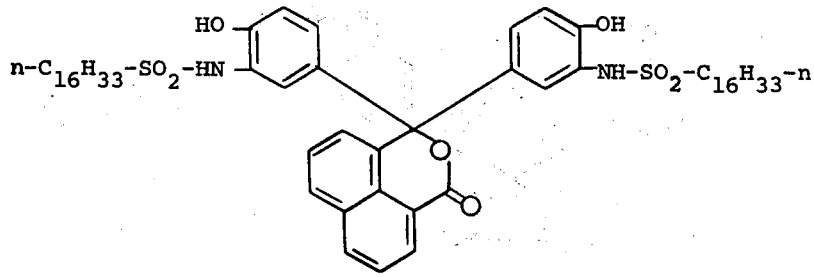
(116)
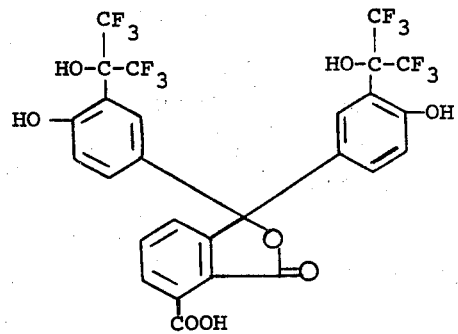

(117)
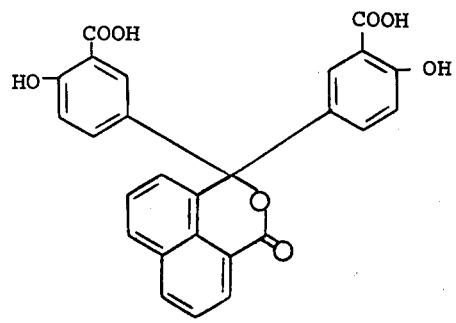
(118)
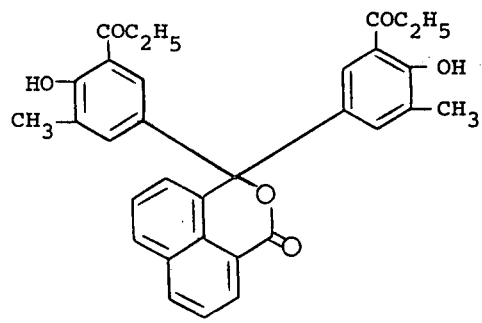
(119)
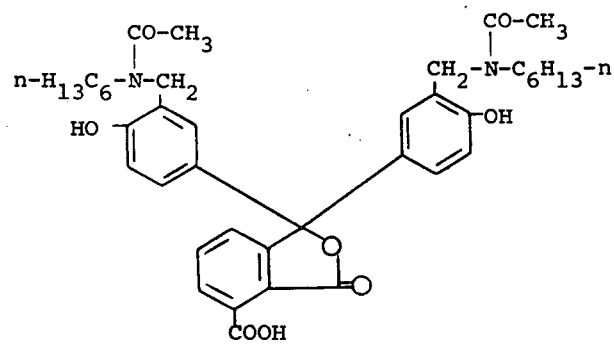
(120)
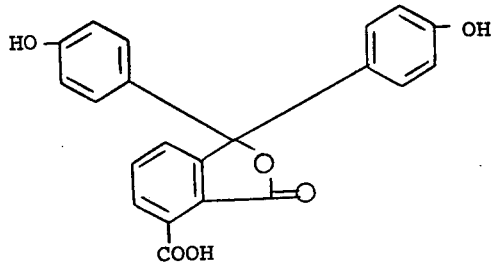

(121)
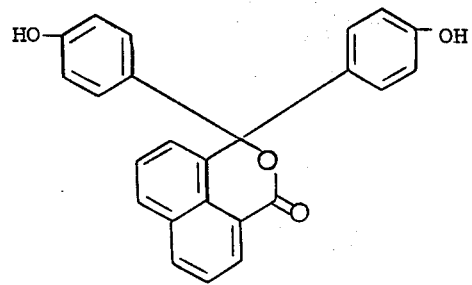
(122)
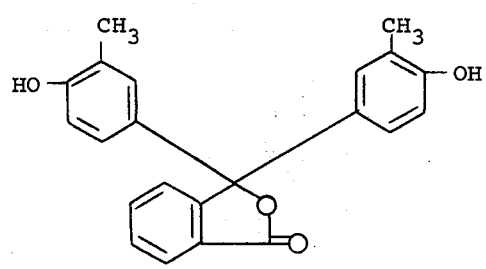
(123)
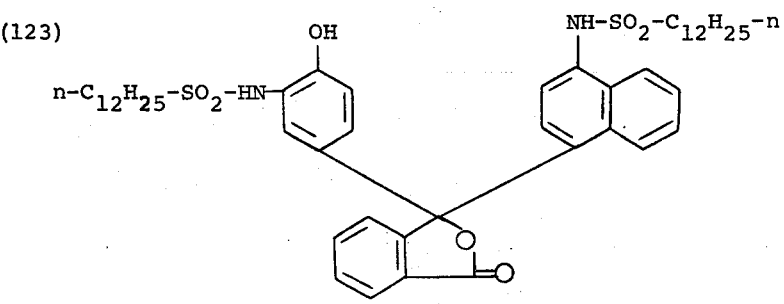
(124)
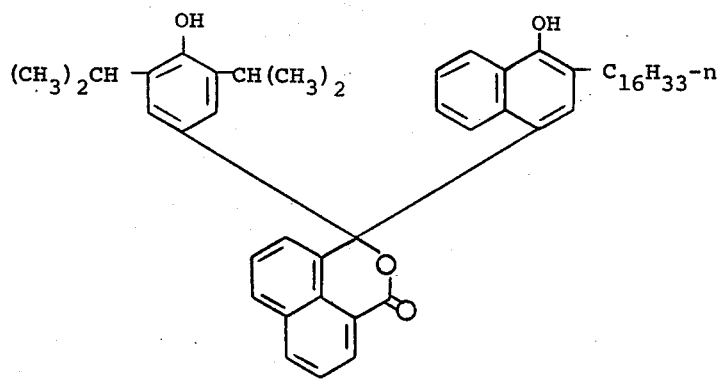
(125)
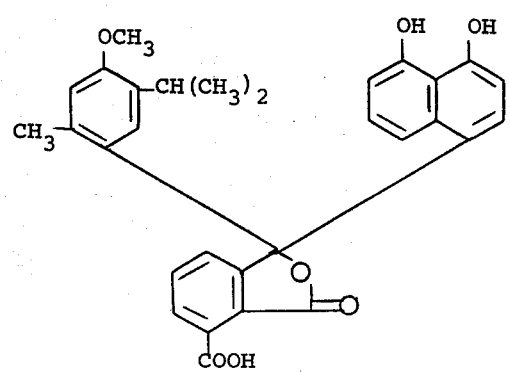

(126)
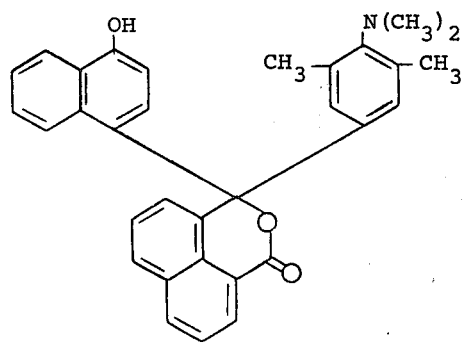
(127)
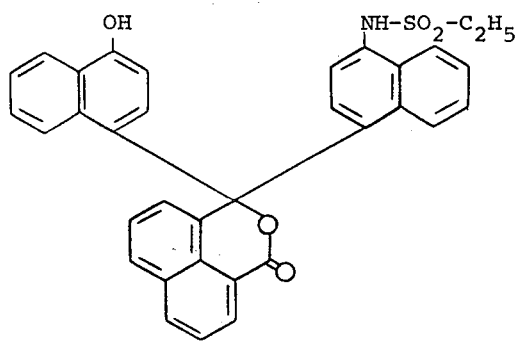
(128)
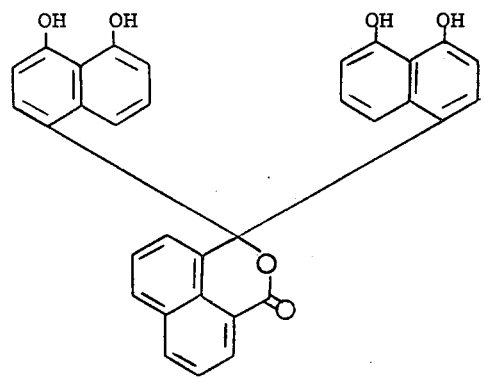
(129)
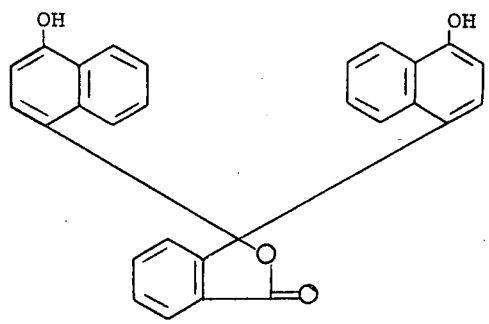

(130) 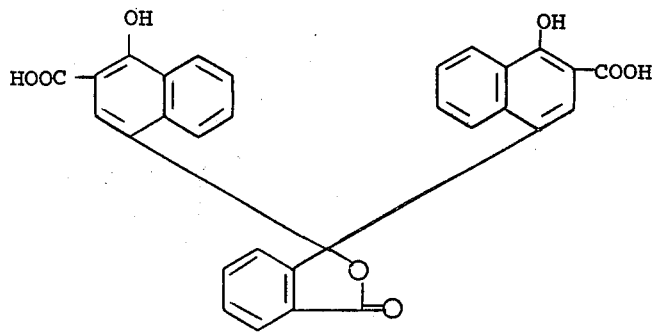
(131) 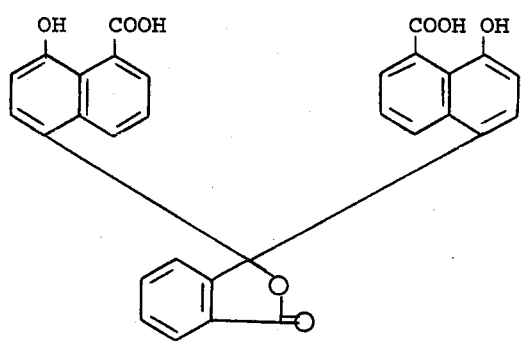
(132) 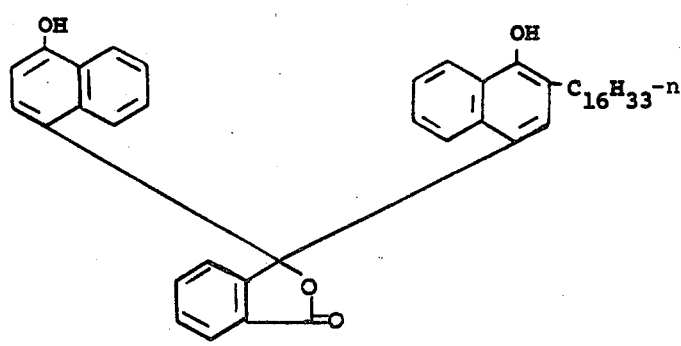
(133) 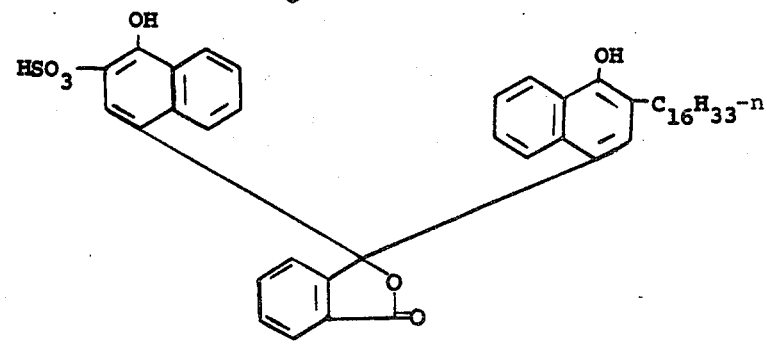
(134) 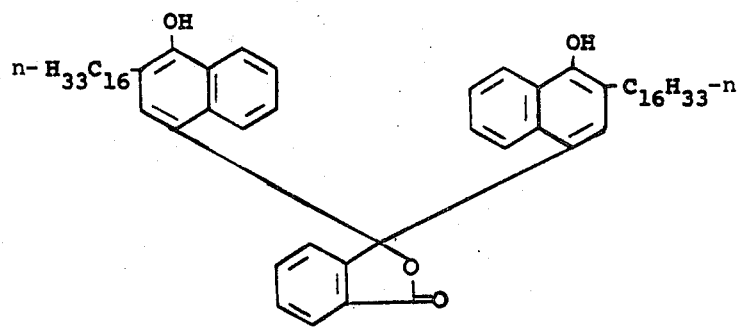

(135) 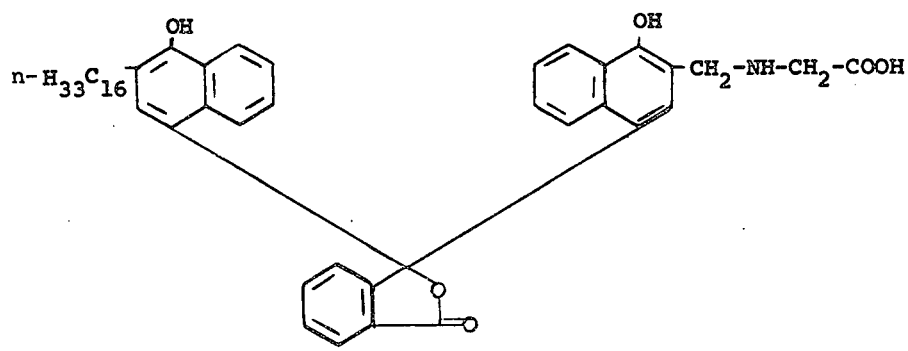
(136) 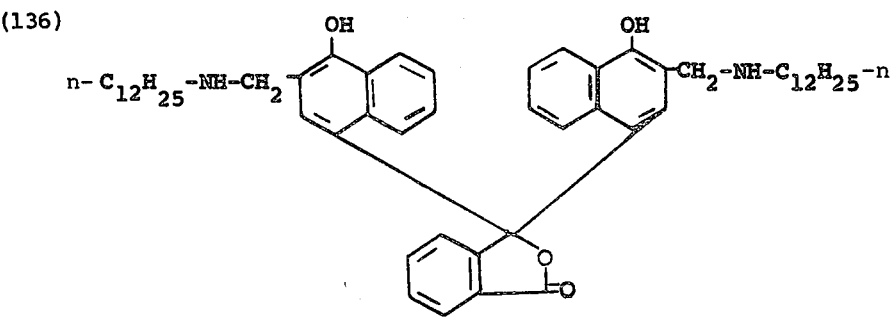
(137) 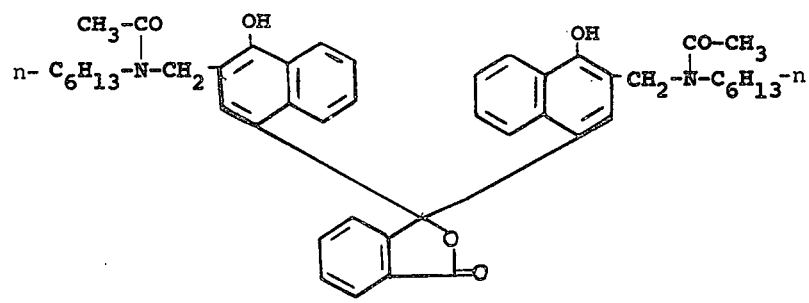
(138) 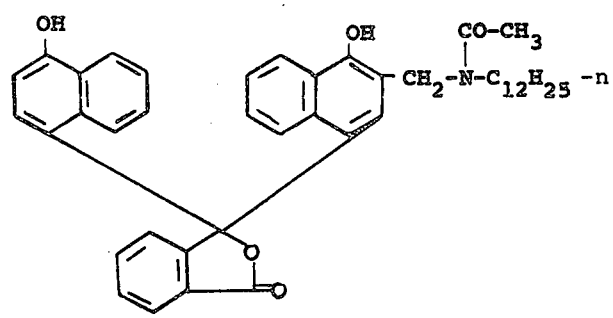
(139) 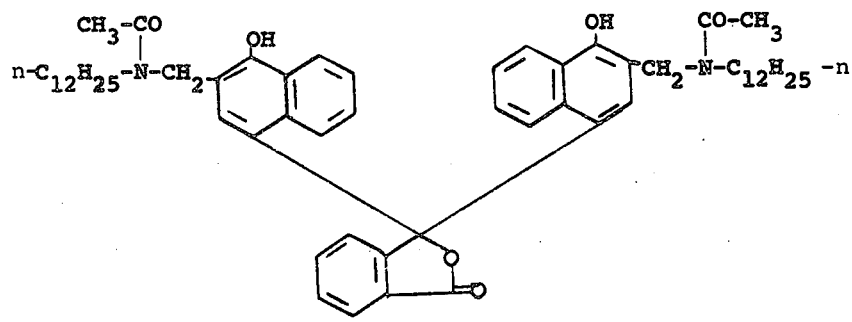

(140)
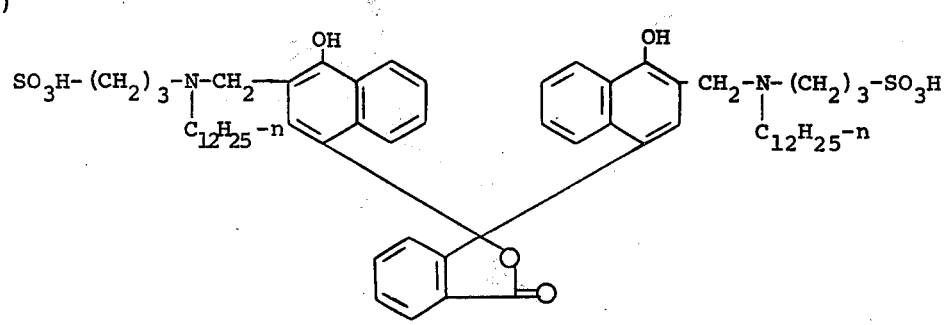
(141)
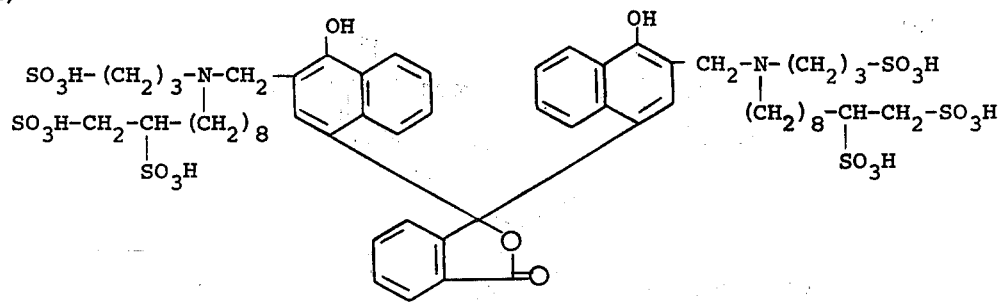
(142)
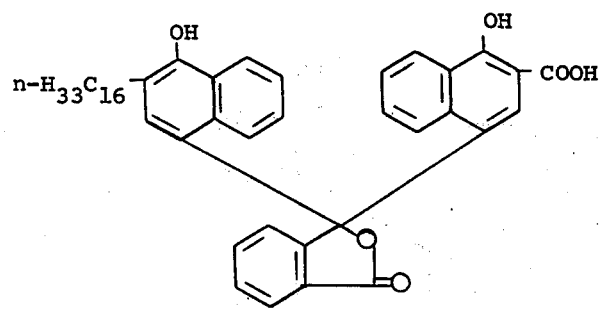
(143)
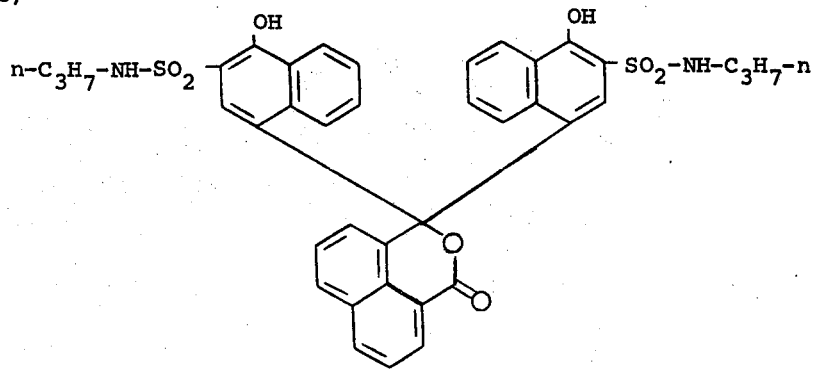

(144)
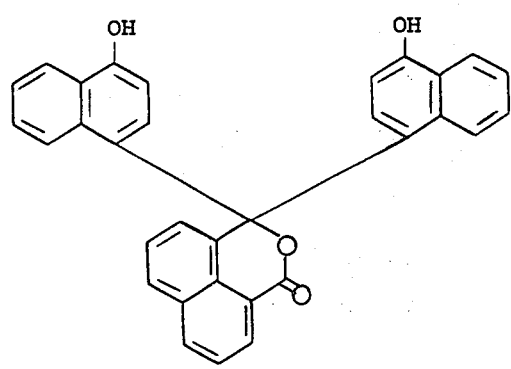
(145)
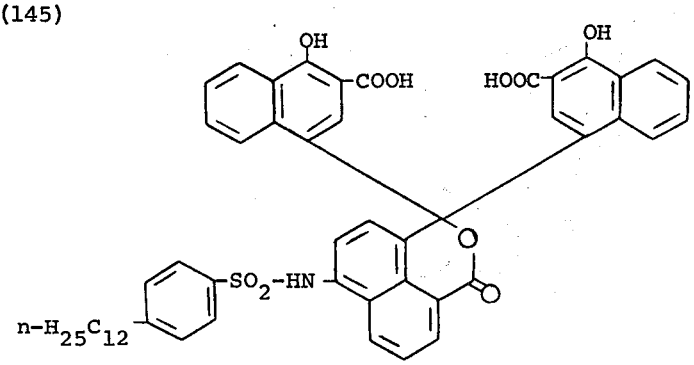
(146)
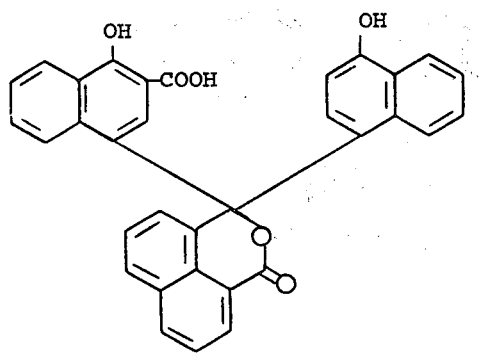
(147)
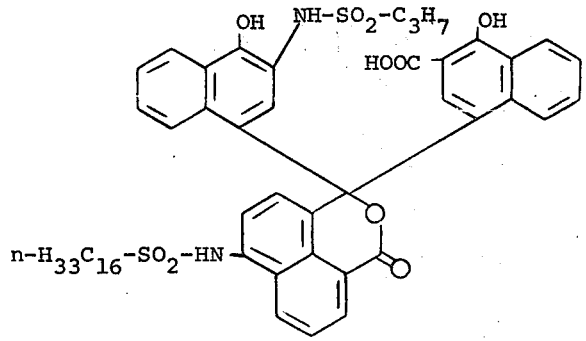

(148)
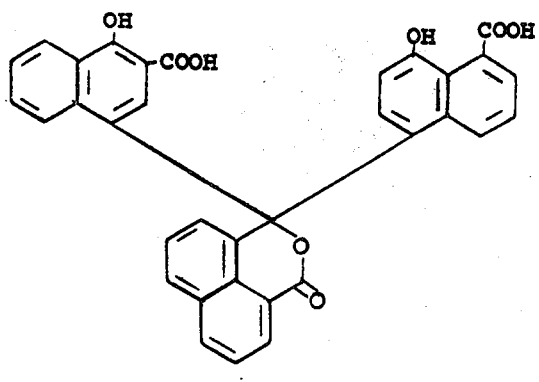
(149)
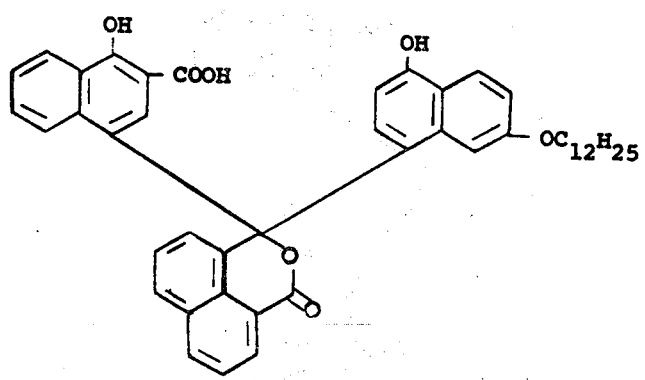
(150)
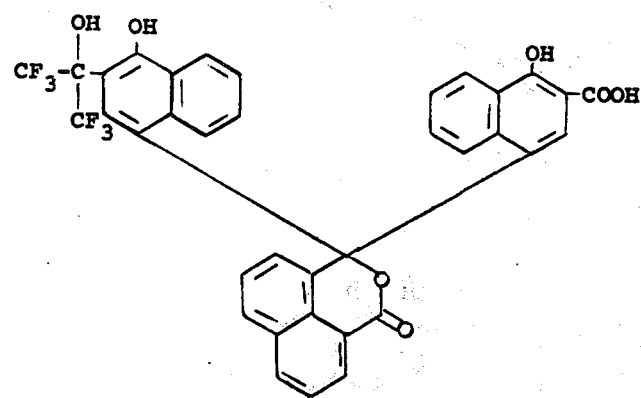
(151)
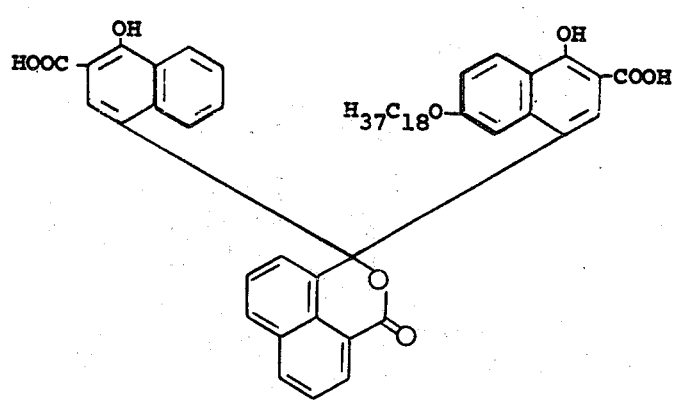

(152) 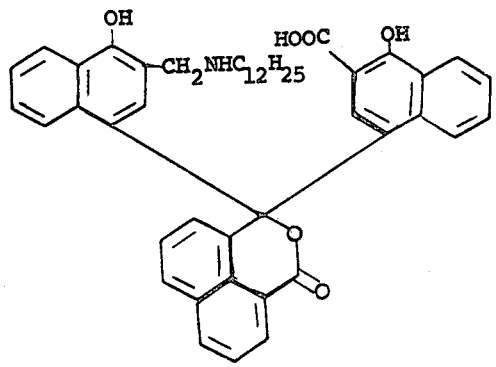
(153) 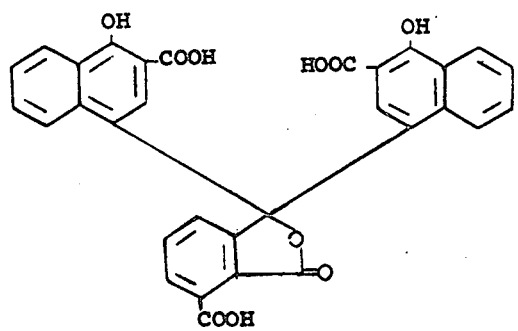
(154) 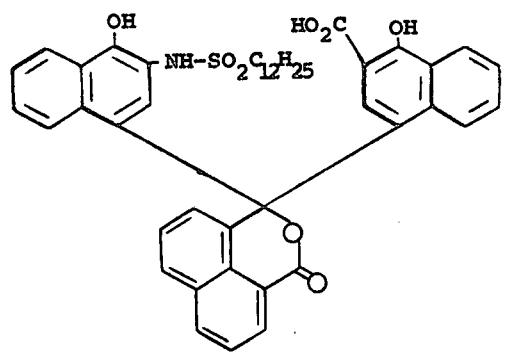
(155) 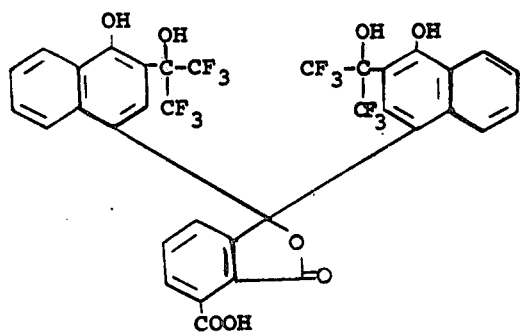
(156) 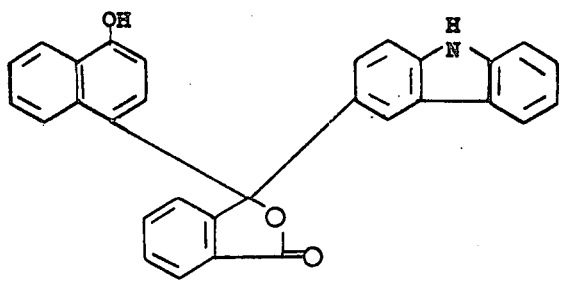

(157) 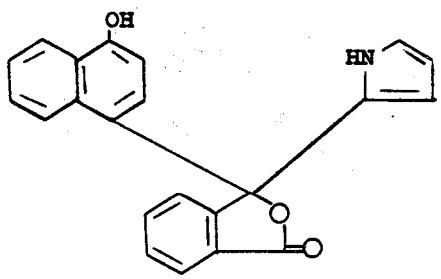
(158) 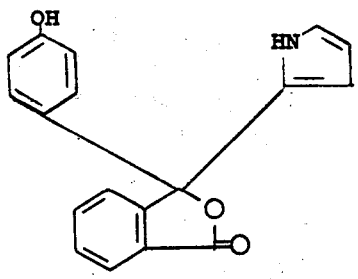
(159) 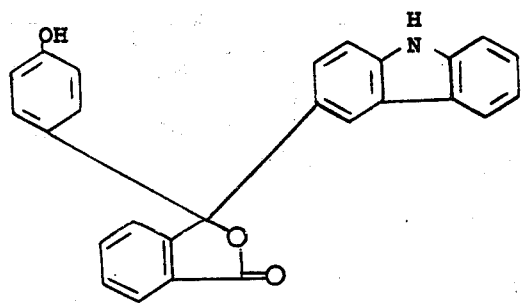
(160) 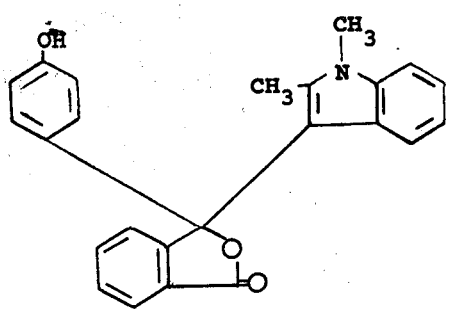
(161) 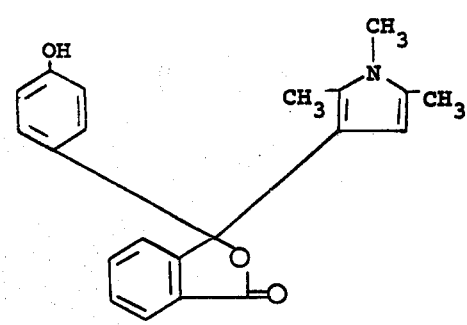

(162) 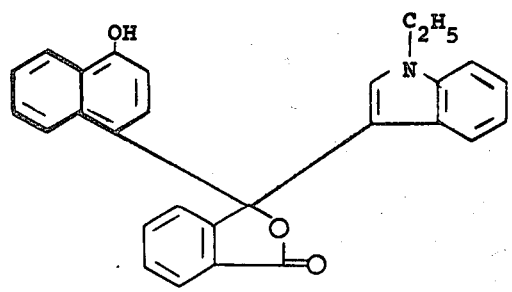
(163) 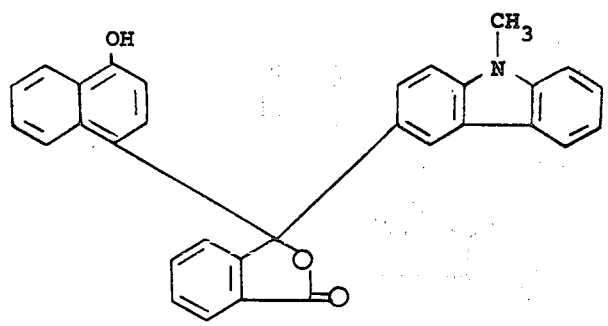
(164) 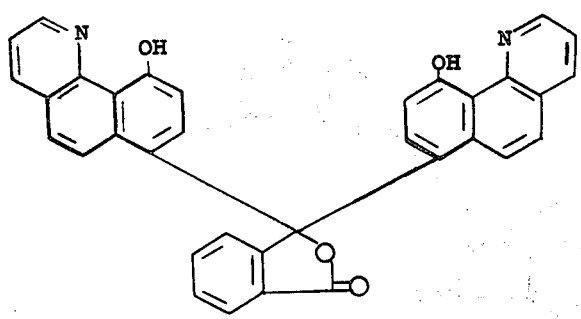
(165) 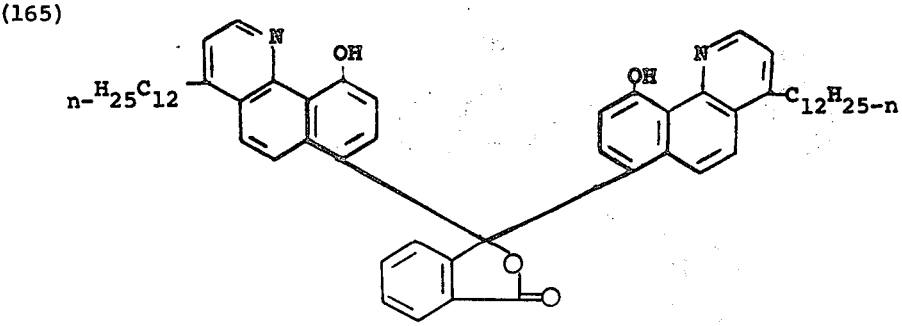
(166) 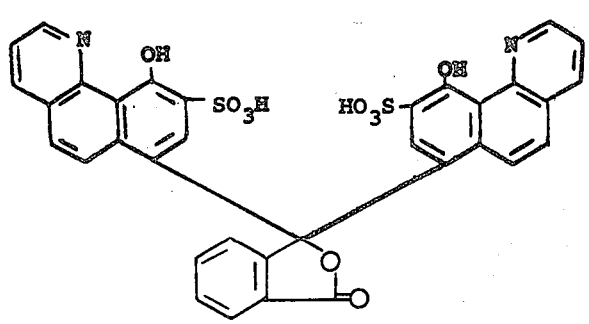

(167) 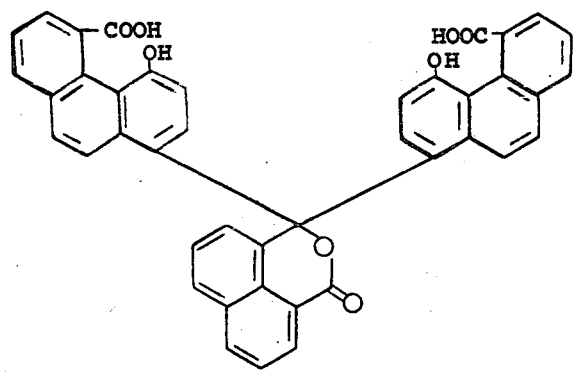
(168) 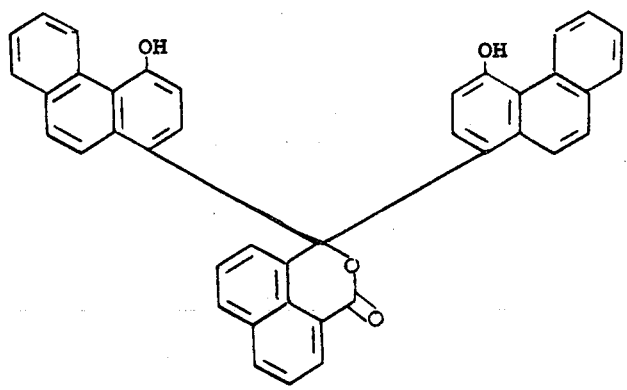
(169) 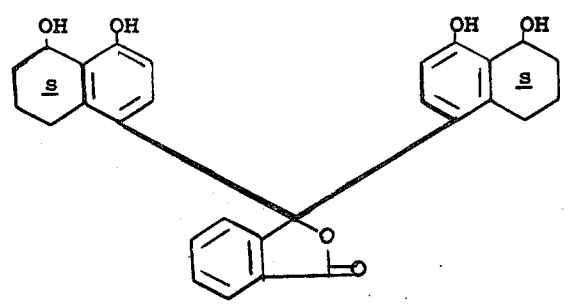
(170) 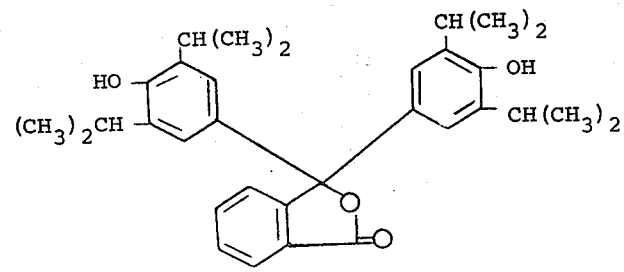
(171) 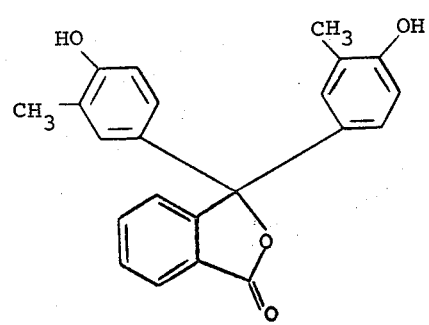

(172)
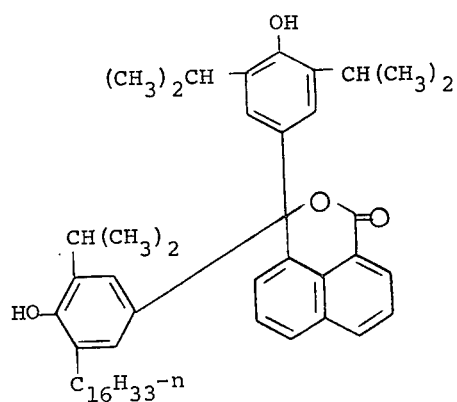
(173)
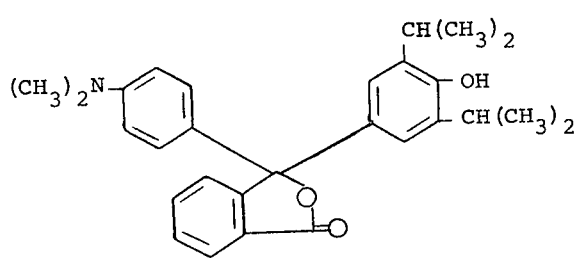
(174)
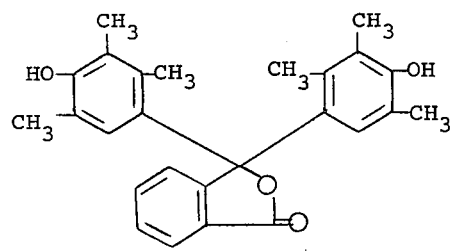
(175)
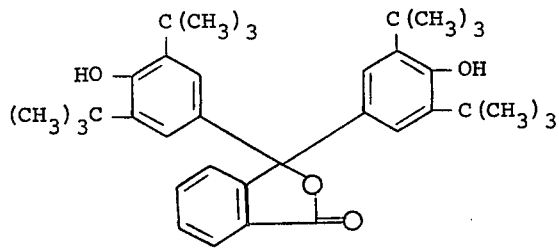
(176)
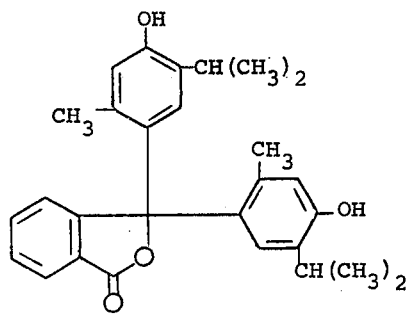

(177) 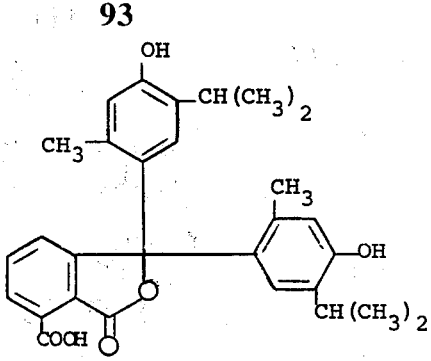

The dehydro and hydrated compounds which may be treated with a protic acid to yield the corresponding protonated compounds of the present invention may be represented by the formulae:

(II) 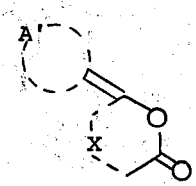

and (III) 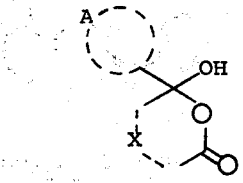

wherein A' is selected from

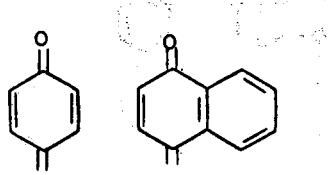

and 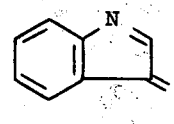 

A is selected from

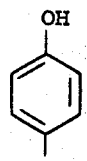 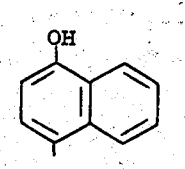 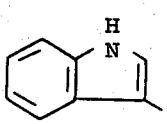

and

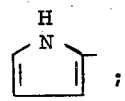

and X represents the atoms necessary to complete a ring-closing moiety selected from phthalide and naphthalide. It will be appreciated that these intermediates may contain one or more substituents as desired in the protonated compounds and as ultimately desired in the complete dye, such as those enumerated above.

As discussed above, the dehydro and hydrated compounds are obtained as the oxidation product of step 2 of aforementioned application Ser. No. 108,662. When the oxidation reaction is carried out under anhydrous conditions, the dehydro intermediate of Formula (II) is obtained and may be isolated, if desired, and reacted with the second aromatic compound to form the complete dye. This intermediate may be readily hydrated to yield the intermediate of Formula (III). Mixtures of the two compounds as represented by Formulae (II) and (III) may be obtained when trace amounts of water are present during oxidation or when the compound of Formula (II) is exposed to atmospheric moisture upon standing. The compound of Formula (III) also may be isolated, if desired, before further reaction. Both intermediates react readily with the aromatic compound, and the product of step 2 may be reacted further without isolating the individual compounds even though the product may be a mixture of the dehydro and hydrated intermediates. Preferably, however, the oxidation reaction is conducted under anhydrous conditions to yield the dehydro intermediate. If it is desired to use the hydrated intermediate for further reaction, it is preferred to hydrate the dehydro compound rather than carrying out the oxidation in the presence of water to yield hydrated intermediate directly.

Specific examples of dehydro and hydrated compounds include:

(178) 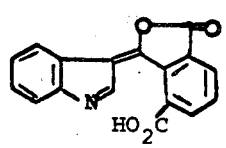

(179) 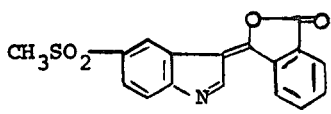
(180) 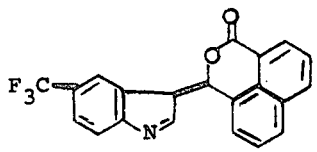
(181) 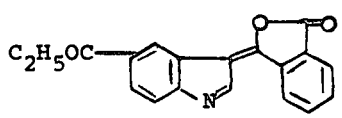
(182) 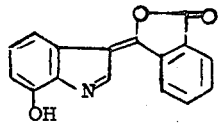
(183) 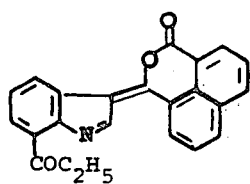
(184) 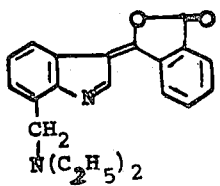
(185) 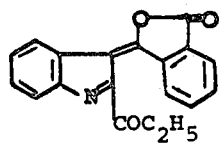
(186) 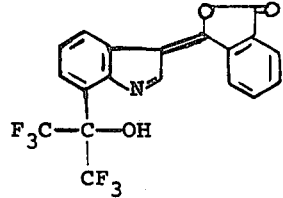
(187) 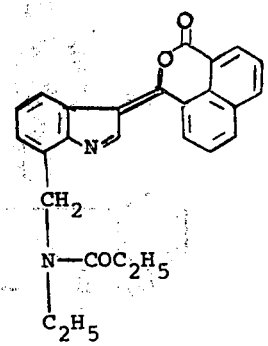
(188) 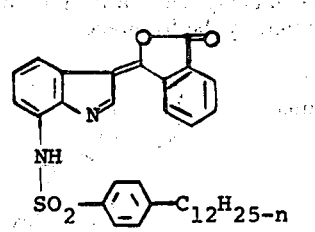
(189) 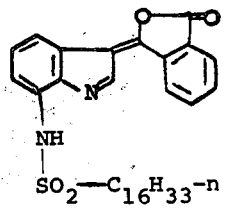
(190) 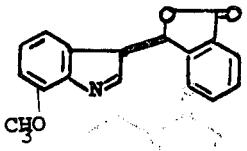
(191) 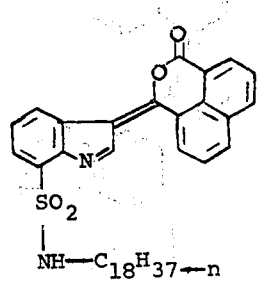
(192) 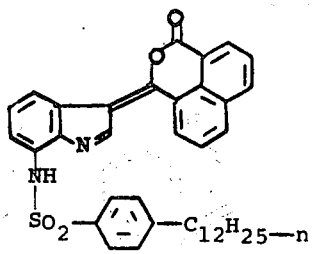

(193) 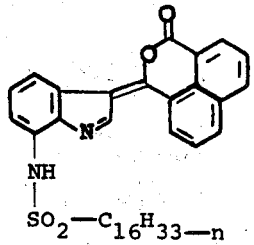
(194) 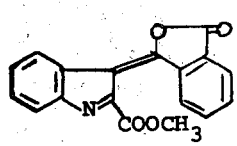
(195) 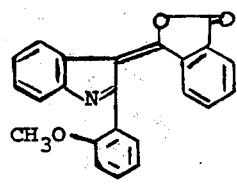
(196) 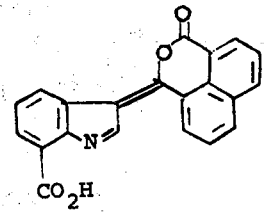
(197) 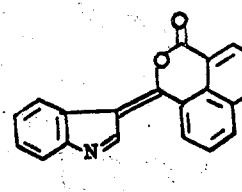
(198) 
(199) 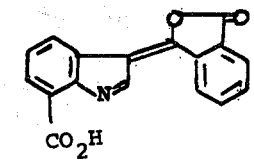
(200) 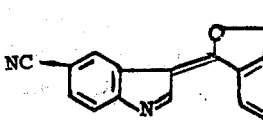
(201) 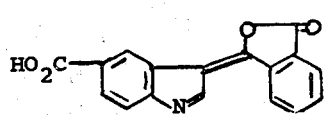
(202) 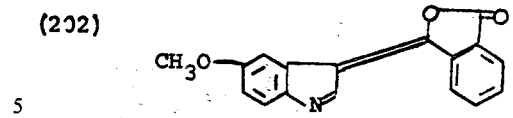
(203) 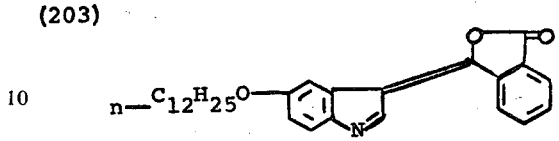
(204) 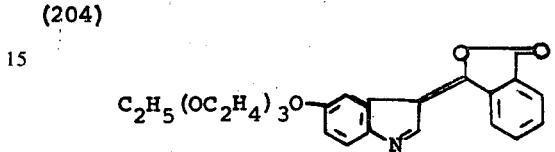
(205) 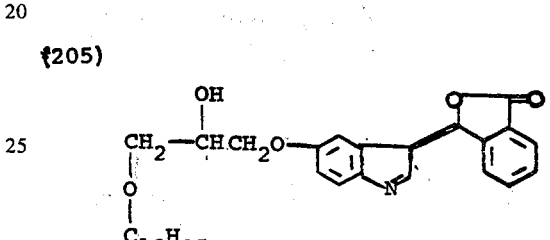
(206) 
(207) 
(208) 
(209) 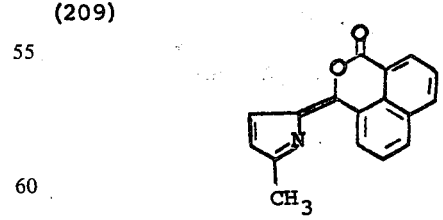
(210) 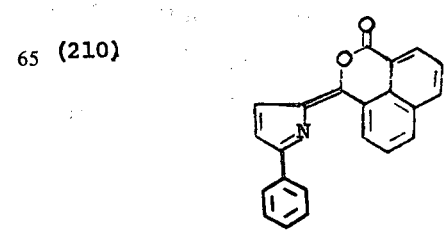

(211) 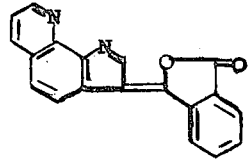
(212) 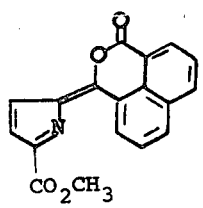
(213) 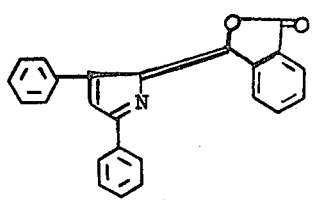
(214) 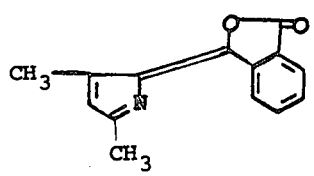
(215) 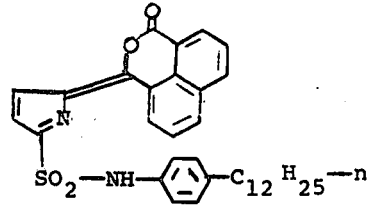
(216) 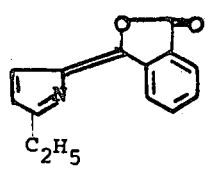
(217) 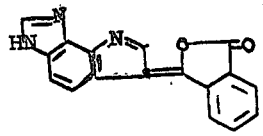
(218) 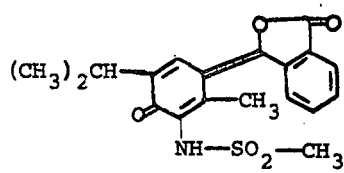
(219) 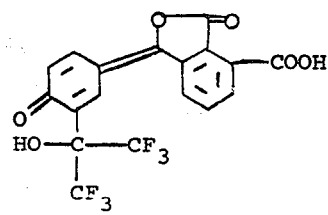
(220) 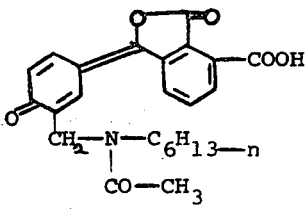
(221) 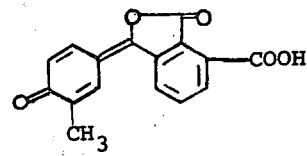
(222) 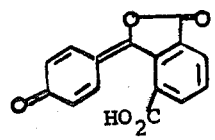
(223) 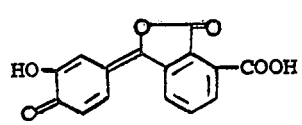
(224) 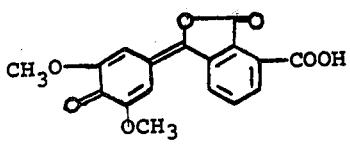
(225) 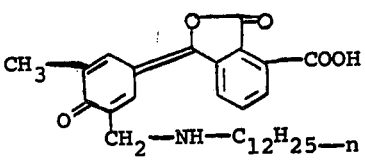
(226) 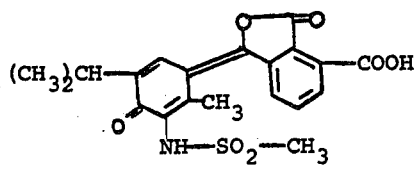

(244) 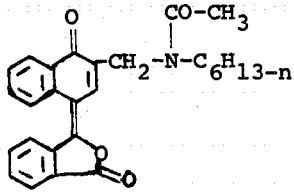
(245) 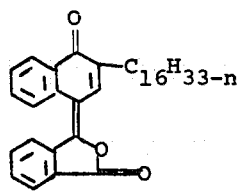
(246) 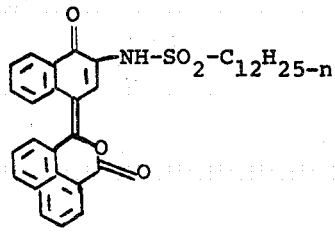
(247) 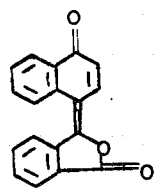
(248) 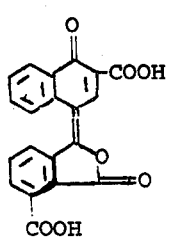
(249) 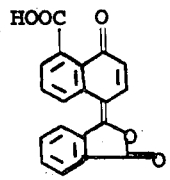
(250) 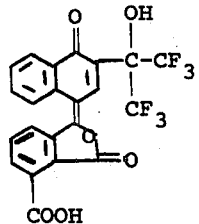
(251) 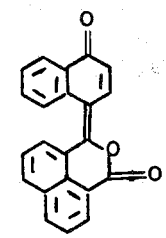
(252) 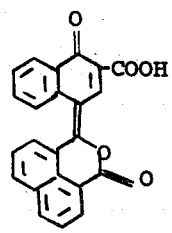
(253) 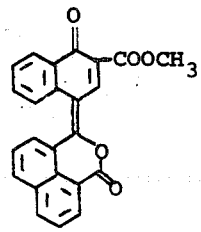
(254) 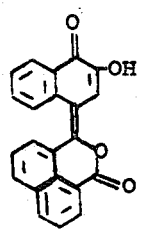
(255) 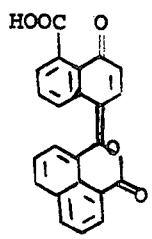
(256) 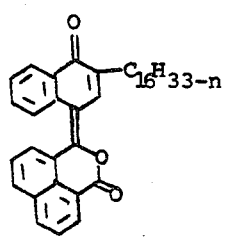

(227) 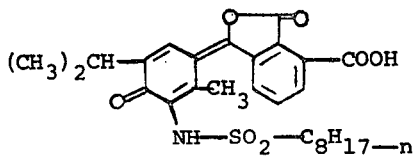
(236) 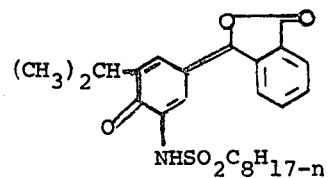
(228) 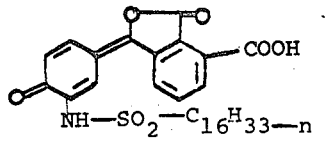
(229) 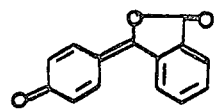
(237) 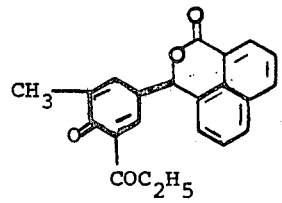
(230) 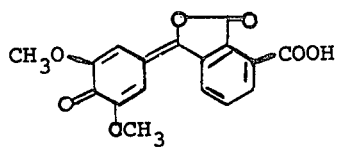
(238)
(231) 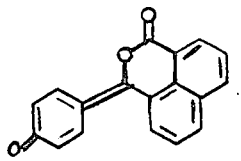
(239) 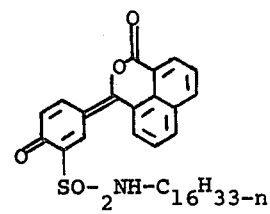
(232) 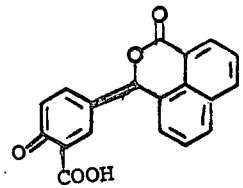
(240) 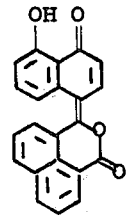
(233) 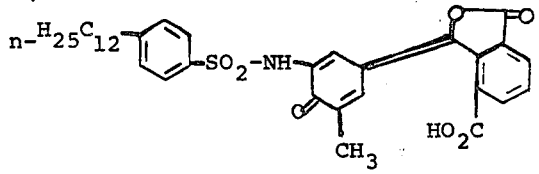
(241)
(234) 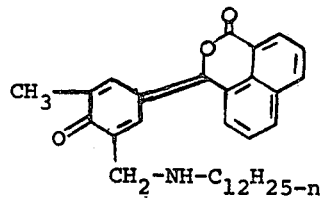
(242) 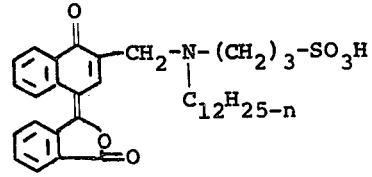
(235) 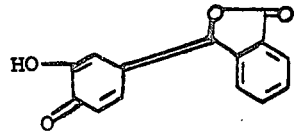
(243) 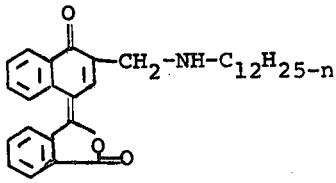

(257) 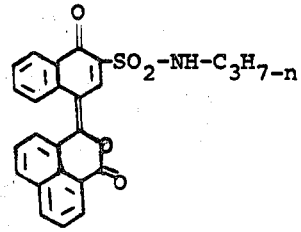
(258) 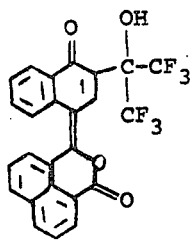
(259) 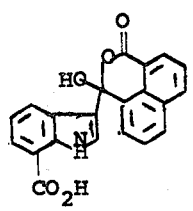
(260) 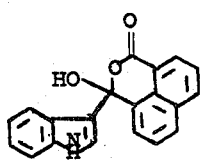
(261) 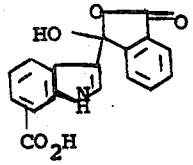
(262) 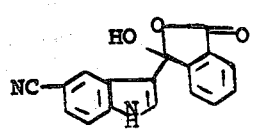
(263) 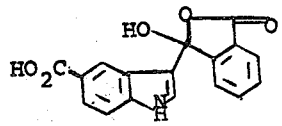
(264) 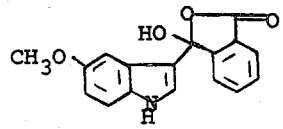
(265) 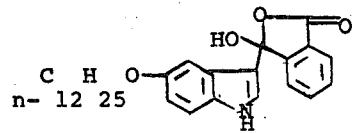
(266) 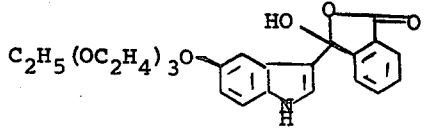
(267) 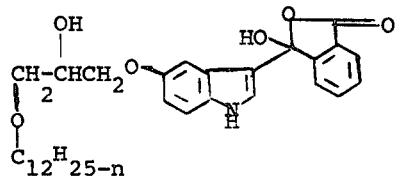
(268) 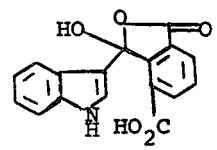
(269) 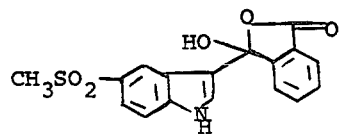
(270) 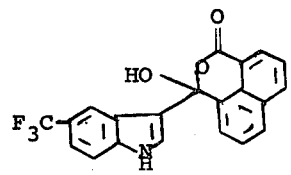
(271) 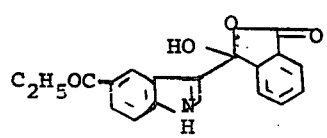
(272) 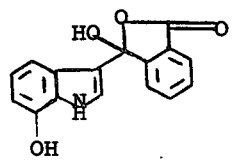
(273) 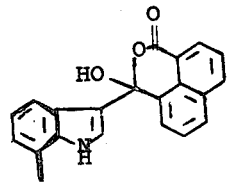
(274) 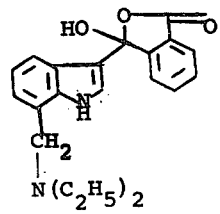

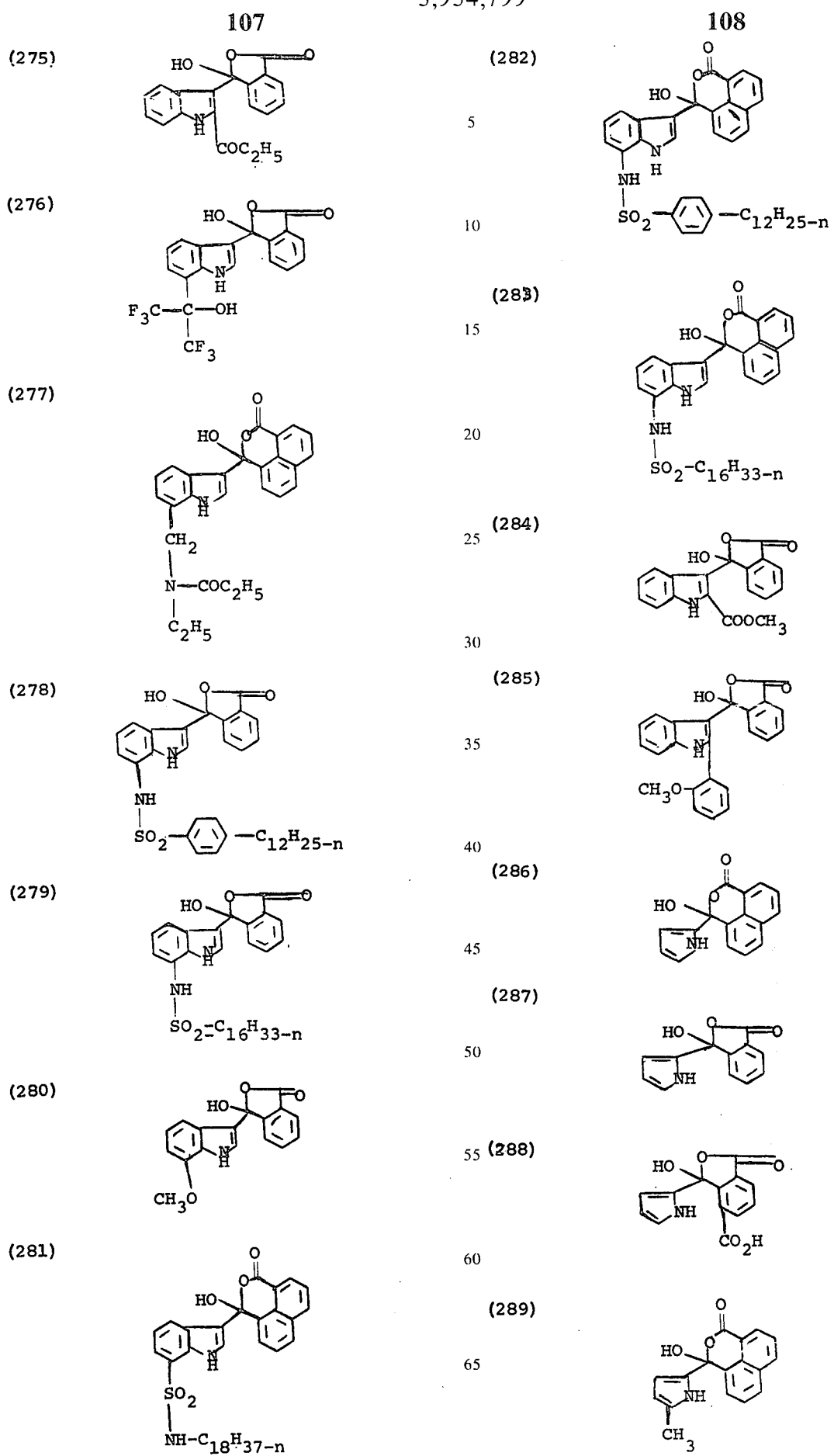

(290) 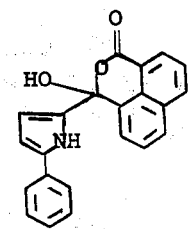
(291) 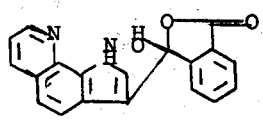
(292) 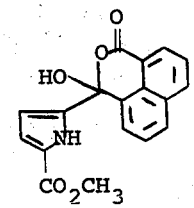
(293) 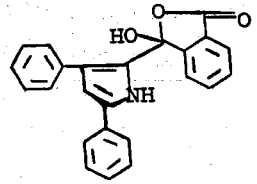
(294) 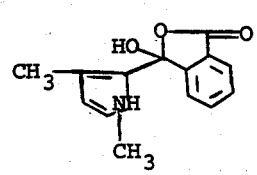
(295) 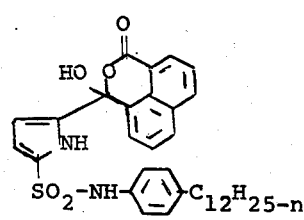
(296) 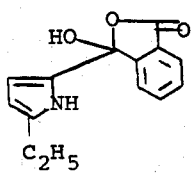
(297) 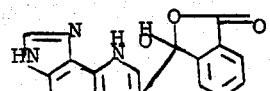
(298) 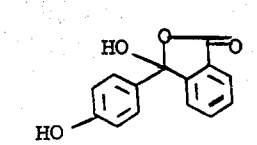
(299) 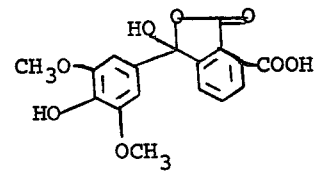
(300) 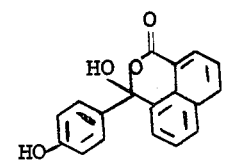
(301) 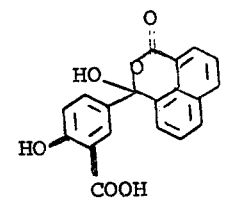
(302) 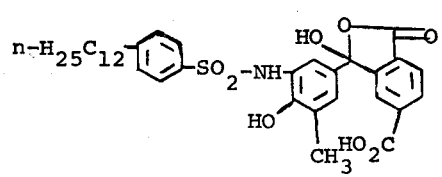
(303) 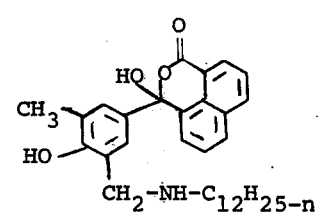
(304) 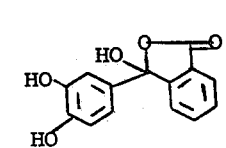
(305) 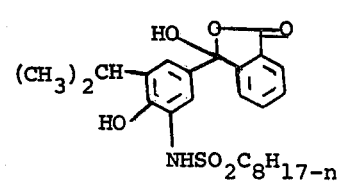
(306) 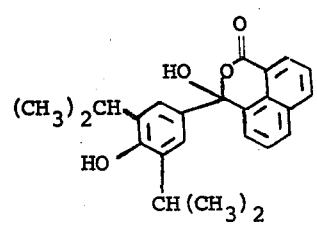

(307) 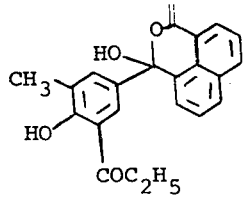
(308) 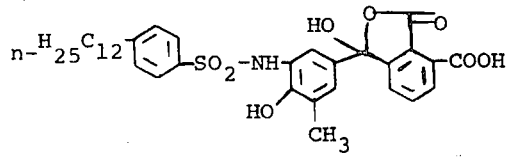
(309) 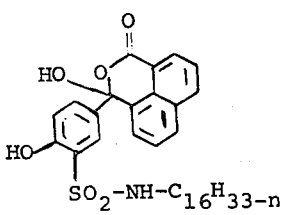
(310) 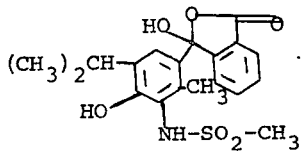
(311) 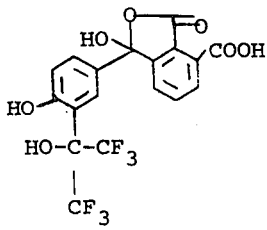
(312) 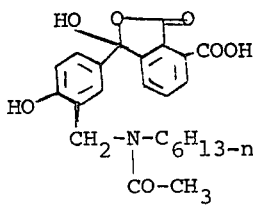
(313) 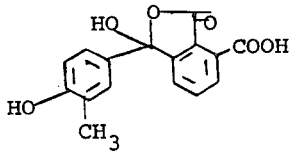
(314) 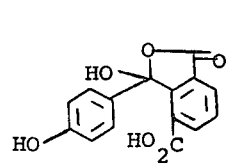
(315) 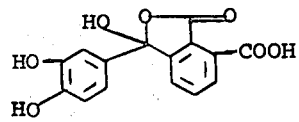
(316)
(317)
(318)
(319)
(320) 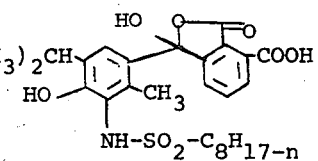
(321) 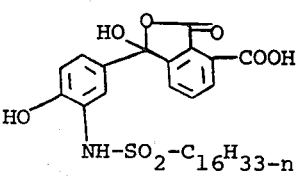
(322) 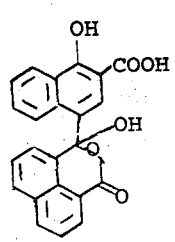

(323) 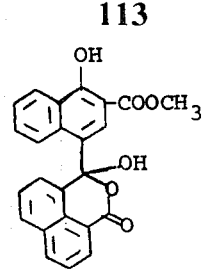
(324) 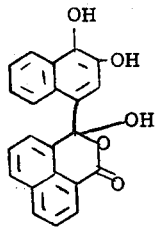
(325) 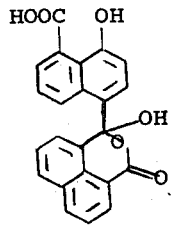
(326) 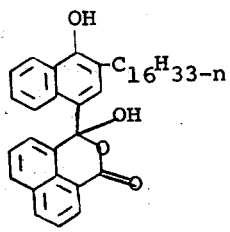
(327) 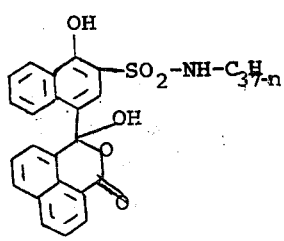
(328) 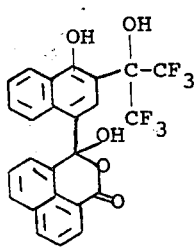
(329) 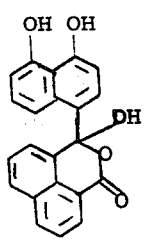
(330) 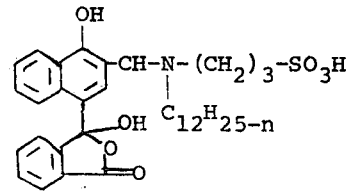
(331) 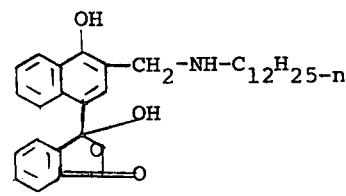
(332) 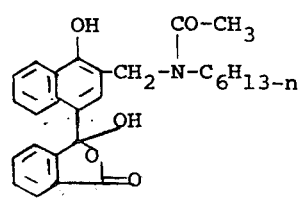
(333) 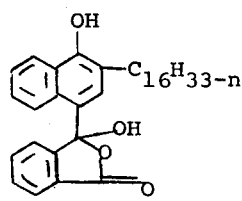
(334) 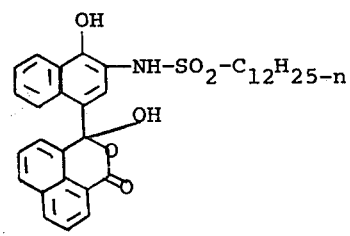
(335) 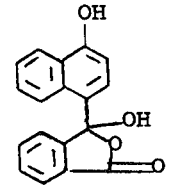
Specific examples of protonated compounds of present invention include:
(336) 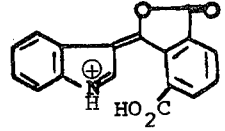
(337) 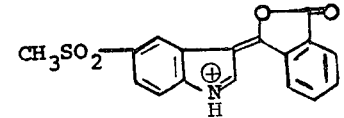

(338) 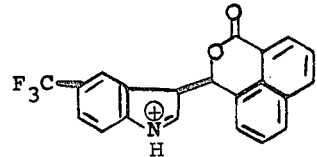
(339) 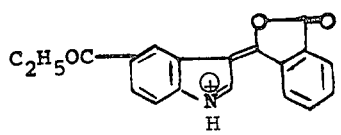
(340) 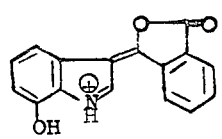
(341) 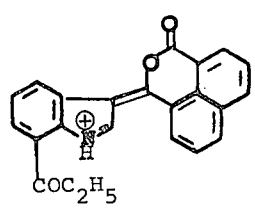
(342) 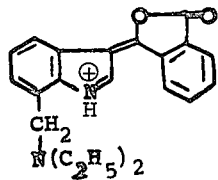
(343) 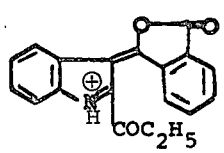
(344) 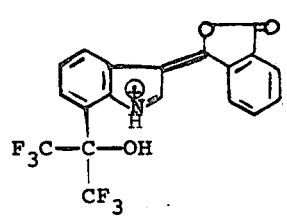
(345) 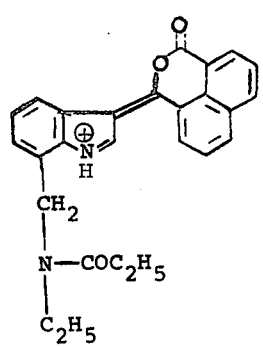
(346) 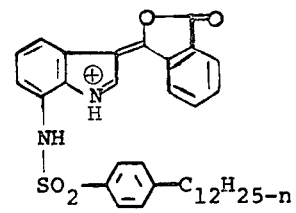
(347) 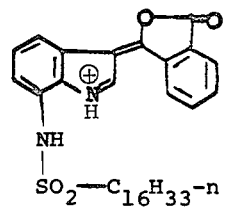
(348) 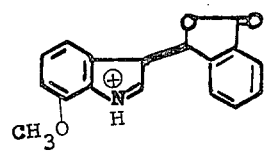
(349) 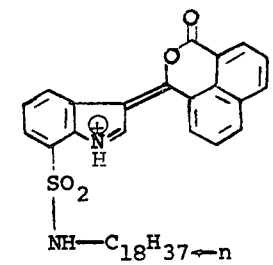
(350) 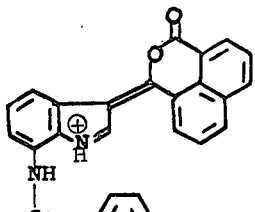
(351) 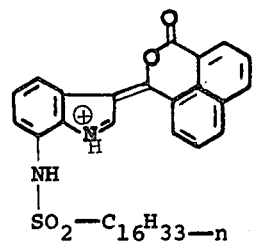
(352) 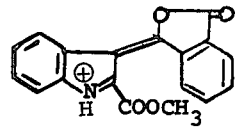

117  118
(353) 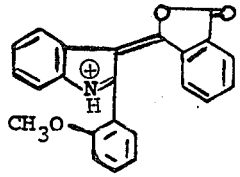   (361) 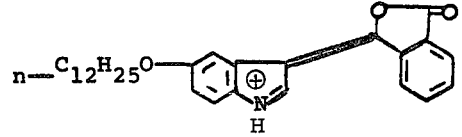
(354) 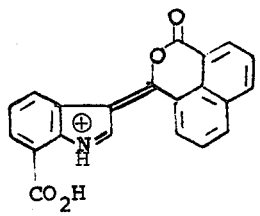   (362) 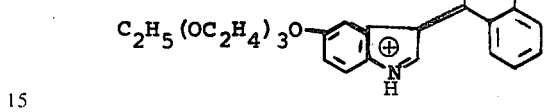
(355) 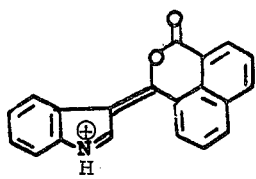   (363) 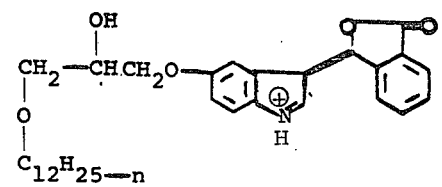
(356) 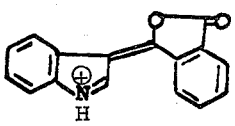   (364) 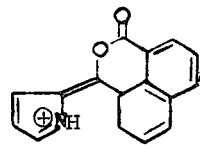
(357) 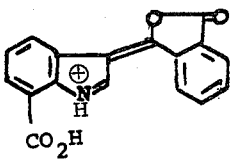   (365) 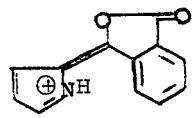
(358) 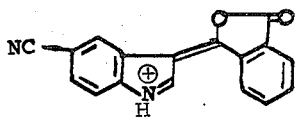   (366) 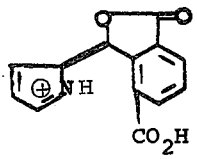
(359) 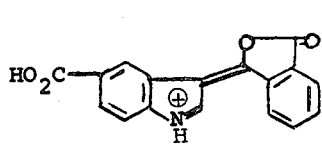   (367) 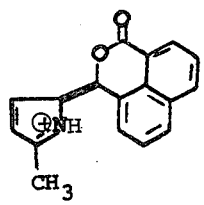
(360) 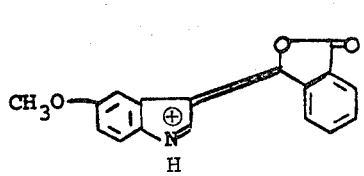   (368) 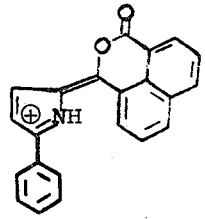

(369) 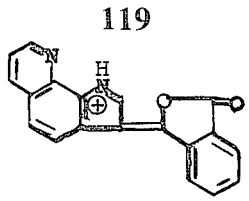
(370) 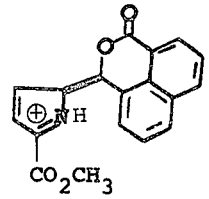
(371) 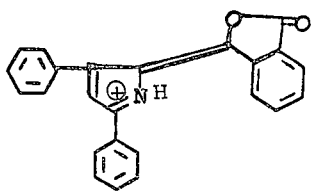
(372) 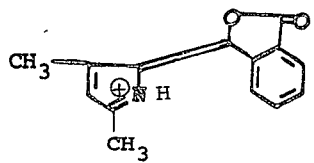
(373) 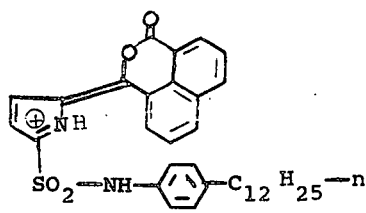
(374) 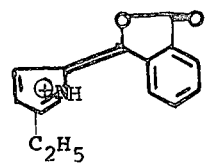
(375) 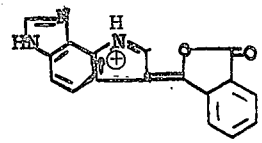
(376) 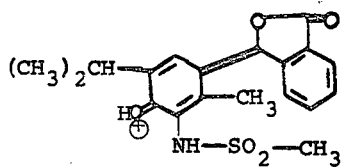
(377) 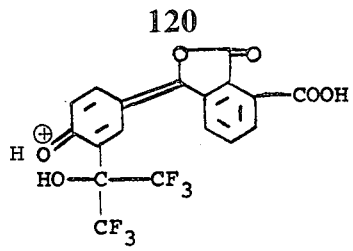
(378) 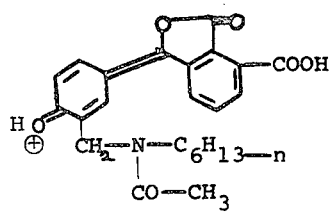
(379) 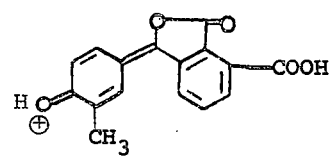
(380) 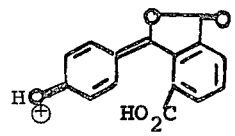
(381) 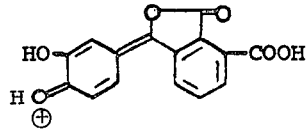
(382) 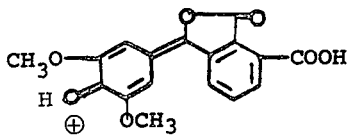
(383) 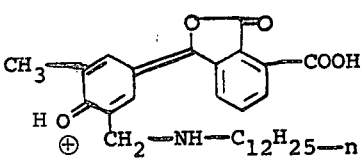
(384) 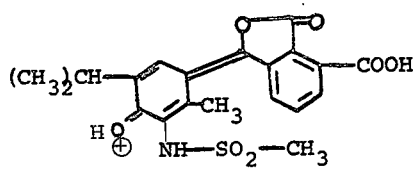

(385) 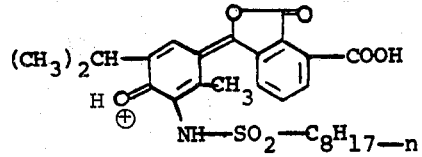
(393) 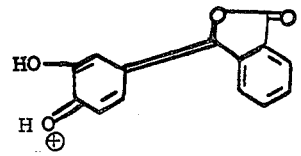
(386) 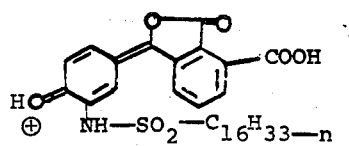
(394) 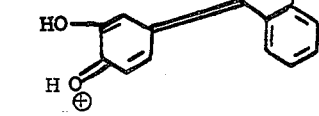
(387) 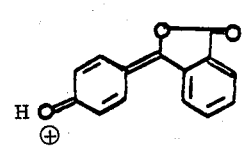
(395)
(388) 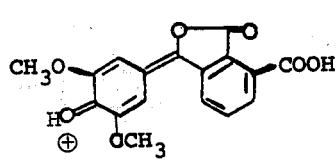
(396)
(389) 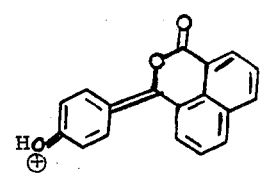
(397)
(390) 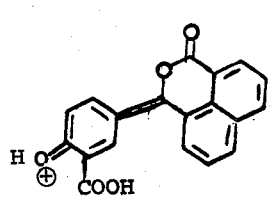
(398)
(391) 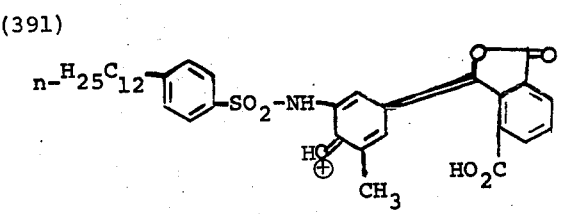
(399)
(392) 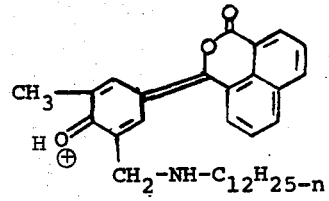
(400) 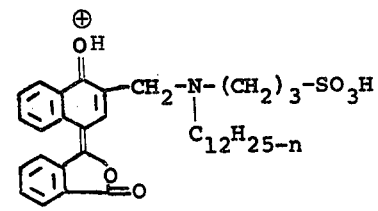

(401) 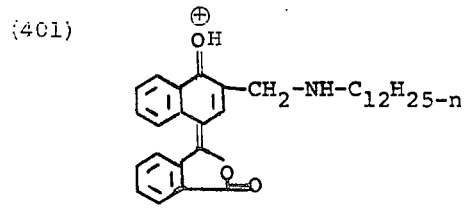
(405) 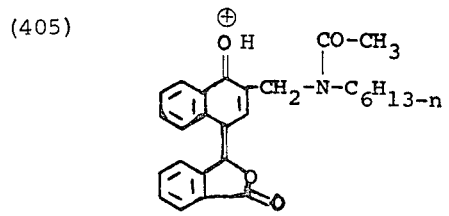
(406) 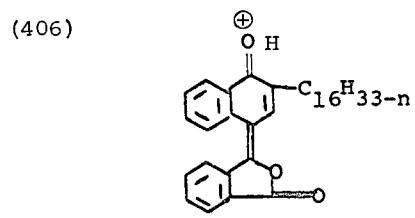
(407) 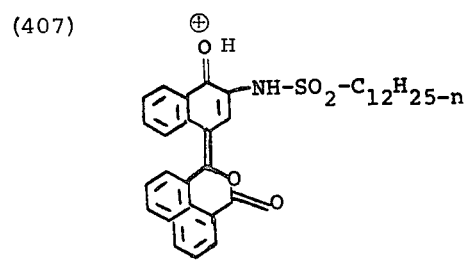
(408) 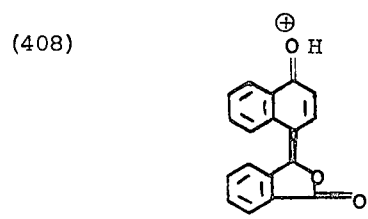
(409) 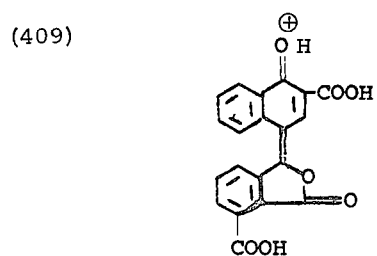
(410) 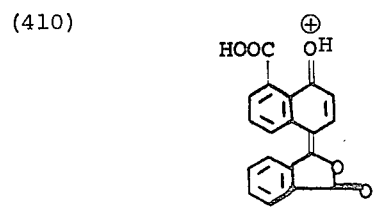
(411) 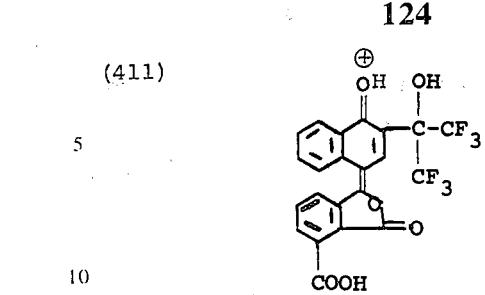
(412) 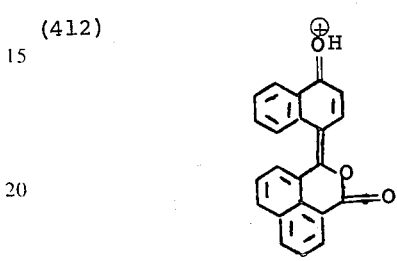
(413) 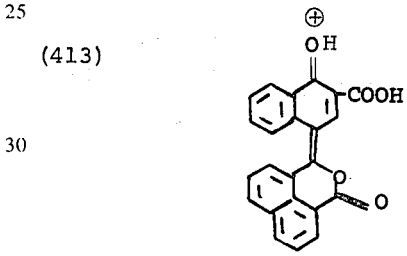
(414) 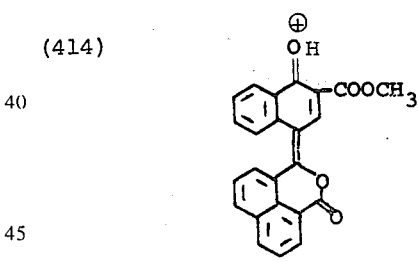
(415) 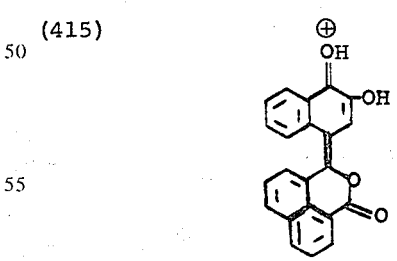
(416) 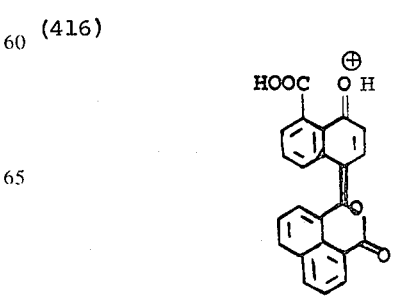

(417) 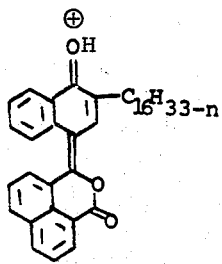

(418) 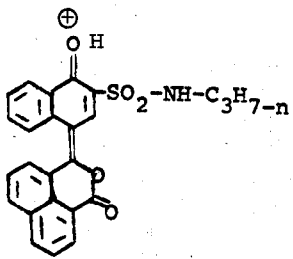

(419) 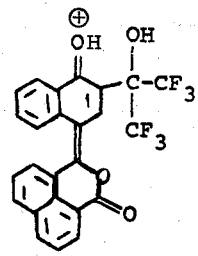

In preparing the subject intermediates, the starting materials, i.e., the hydroxy substituted carbocyclic compound or N-heterocyclic compound and the (na)phthalaldehydic acid may be reacted in a solvent at room temperature or elevated temperature as described in the aforementioned reference of Rees et al. In the present invention, it is sometimes preferred to react the starting materials in the presence of an external acid catalyst, for example, an organic acid catalyst, such as toluene-p-sulfonic acid, trifluoroacetic acid and trichloroacetic acid. The reaction temperature may vary over a relatively wide range from room temperature, i.e., about 20° C. up to elevated temperatures of about 120°C. which may be readily determined for the particular reactants. To achieve practical reaction rates, it is preferred to conduct the reaction at elevated temperatures but below temperatures where decomposition of starting material and/or side reactions and by-products tend to occur. The solvent used may be any of the inert organic liquids commonly employed for this purpose, such as, glacial acetic acid, ethanol, propanol, petroleum ether, hexane, heptane, cyclohexane, toluene, methylene chloride, and benzene. Ordinarily, a polar solvent is selected when an external acid catalyst is employed and a non-polar solvent when the reaction is conducted in the absence of an external acid catalyst.

The (na)phthalidyl intermediate of the phenol, naphthol, indole or pyrrole thus produced is oxidized by dehydrogenation to selectively remove the hydrogen from the 3-position of the (na)phthalidyl portion and to remove the hydrogen from the hydroxy group of the phenol (or naphthol) or from the 1-position, i.e., N atom of the indole (or pyrrole) thereby converting the single bond connecting the two portions of the molecule to a double bond. Quinones have been found particularly useful for this purpose including, for example, ortho- and para-quinones, such as dicyanodichloroquinone, chloranil, and ortho-chloranil. It has been found that these materials will selectively remove the hydrogens as desired and without oxidizing the compound further. The solvent used in the oxidation step may be any inert organic liquid that does not react with the oxidizing agent, such as dioxane, toluene, benzene, dichloromethane and hexane. The temperature employed may vary widely and generally ranges between about 20°C. and 200°C. As in the initial condensation step, the oxidation step is preferably conducted at elevated temperatures that may be readily selected to achieve a practical reaction rate without by-product formation.

As discussed previously, the dehydro and hydrated oxidation products may be reacted with a protic acid under anhydrous conditions at a temperature between about 50° and 200°C. to yield the corresponding protonated compound. In the preparation of indicator dyes, a second aromatic compound is condensed with the protonated compound to yield the complete indicator dye. The second condensation reaction, like the initial condensation is carried out in a suitable solvent at room or elevated temperatures of about 20° to 120°C. and, if desired, may be conducted in the presence of an acid catalyst such as phosphorous oxychloride, boron trifluoride (e.g., in benzene or ether) and other Lewis acids, such as zinc chloride and the catalysts enumerated above, i.e., toluene-p-sulfonic acid, trifluoroacetic acid and trichloroacetic acid. The inert organic solvent used may be any of those commonly employed in condensation reactions such as the particular solvents mentioned above for use in the initial condensation.

In another embodiment, as discussed above, the protonated compound may be formed in situ in the condensation reaction by employing a protic acid, e.g., toluene-parasulfonic acid as the catalyst in the condensation of the aforementioned oxidation product(s) and second aromatic compound. Though the protonated compound may be generated in situ from either the hydrated or dehydro oxidation product, it is preferred to use the dehydro form so that water will not have to be removed during the course of the reaction.

The starting materials preferably are used in equimolar quantities and in the oxidation step, the oxidizing agent and (na)phthalidyl intermediate may be used in equimolar quantities but preferably, the oxidizing agent is used in excess to ensure completion of the reaction. A ratio of 1.1 to 1.5 moles of oxidizing agent to 1.0 mole of intermediate has been found satisfactory. In the second or final condensation, the oxidized intermediate and the second aromatic compound selected to form the complete dye preferably are used in equimolar proportions.

As the starting materials, any phenol or 1-naphthol may be employed provided it has a free 4-position, i.e., it is unsubstituted on the carbon atom para to the phenolic hydroxy group, so that the hydrogen will be displaced to yield the corresponding 4-(na)phthalidyl intermediate in the initial condensation with the acid. Likewise, any indole or pyrrole starting material may be employed provided that these compounds have a free 3-position and a free 2-position, respectively, so that the corresponding 3-(na)phthalidylindole and 2-(na)phthalidylpyrrole will be produced in the initial condensation reaction. The indoles and pyrroles each should also have a free 1-position, i.e., the nitrogen atoms of these compounds should be substituted with hydrogen. Other than the necessary free positions discussed above, the starting materials may contain one or more substituents as may be desired in the final indicator dye provided any substituent positioned adjacent the condensation site and tending to bond internally with the dehydro intermediate is protected with a blocking group that may be removed subsequent to condensation of the intermediate with the second aromatic compound. For example, the carboxy group of 2-carboxyindole may be protected as an alkyl ester and the alkyl blocking portion removed after the complete dye is formed by alkaline hydrolysis. Similarly, a hydroxysubstituted aryl or alkyl group in the 2-position of an indole may be protected as an alkyl ether and the alkyl blocking portion removed by catalytic hydrogenation.

For purposes of nomenclature, the following illustrates the numbering of the hydroxy-substituted carbocyclic compounds and N-heterocyclic compounds used as the starting materials in the present method

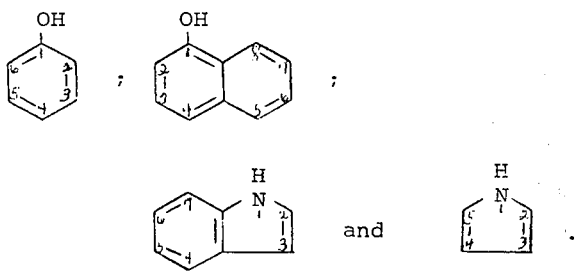

Likewise, the aldehydic acid reacted with the hydroxy-substituted carbocyclic or N-heterocyclic compound may be a substituted phthalaldehydic acid or naphthalaldehydic acid, such as, carboxy-substituted compounds, e.g., 4-carboxy-phthalaldehydic acid and 7-carboxy-phthalaldehydic acid and sulfonamido-substituted compounds, e.g., 6-hexadecylsulfonamidonaphthalaldehydic acid.

The aromatic compound condensed with the oxidized intermediate to form the complete dye may be a carbocyclic aryl compound of the benzene or naphthalene series, or it may be a heterocyclic aryl compound containing O, N, S, or P or combinations thereof. The heterocyclic compound is preferably N-heterocyclic derived from, e.g., indole, pyrrole or carbazole, though it may be derived from, e.g., N-benzylindoline.

The following Examples are given to further illustrate the present invention and are not intended to limit the scope thereof.

EXAMPLE 1

Preparation of the compound of formula (21):

A mixture of 6.0 g. (0.0372 mole) of 7-carboxyindole and 7.5 g. (0.0372 mole) of naphthalaldehydic acid in 38 ml. of glacial acetic acid was heated to reflux and stirred mechanically. To the solution was added dropwise, 38 ml. of 12% toluene-p-sulfonic acid-acetic acid. An immediate precipitation of product began and the mixture was refluxed for five minutes. The mixture was cooled to room temperature, filtered, and the 3-naphthalidylindole intermediate washed with 50 ml. of acetic acid. The solid was then stirred in 100 ml. of acetone, filtered and dried to give 12.8 g. (86% by weight yield) of a white crystalline solid, 239°–240°C. melting range.

A mixture of 11.0 g. (0.028 mole) of the intermediate prepared above and 140 ml. of dioxane was refluxed with stirring under nitrogen. To the solution was added 7.3 g. (0.032 mole) of 2,3-dichloro-5,6-dicyano-1,4-benzoquinone and the refluxing continued for 3.5 hours. The mixture was cooled to room temperature and the pink solid comprising oxidized intermediate was collected by suction filtration. The solid was extracted twice by boiling in 125 ml. of acetone for 5 to 10 minutes. The solid was then heated in 125 ml. of ethanol and the white solid collected. Weight 7.2 g. (78% by weight yield).

A mixture of 0.40 g. (1.2 m mole) of oxidized intermediate and 0.51 g. (1.2 m mole) of 7-hexadecylsulfonamidoindole in 5 ml. of glacial acetic acid was heated to 65°C. with stirring. To the mixture was added 5 ml. of 12% toluene-p-sulfonic acid-acetic acid over a five-minute period. The solution turned an intense purple color. The heating was continued for 15 minutes at 65°C. and cooled to room temperature. The solution was poured into 20 ml. of water containing 3 ml. of concentrated $NH_4OH$. The precipitate was collected and dried. Recrystallization of 0.8 g. of this material from methanol-water gave 0.66 g. (77% by weight yield) of title compound, melting range 216°–217°C.

Steps 1 and 2 of the foregoing procedure were repeated using 2-carboxy-benzaldehyde (o-formylbenzoic acid), the open-ring form of phthalaldehydic acid.

8.05 g. (0.05 mole) of 7-carboxyindole and 7.5 g. (0.05 mole) of 2-carboxybenzaldehyde were heated under reflux in 90 ml. of xylene in a 500 ml. roundbottom flask with stirring for 8 hours. The mixture was cooled to room temperature and allowed to stand overnight. The product was collected by suction filtration, washed with benzene and dried in vacuo at 60°C. Wgt. = 13.0 g. The product was recrytallized from ethanol (~ 300 ml.). After refrigeration, the product was collected by suction filtration. Wgt. = 8.2 g., melting range 250°–2°C. The ethanol was evaporated to ~ 50 ml. and a second crop of material collected. Wgt. = 2.0 g., melting range 248°–50°C. Overall yield 10.2 g., (67% by weight yield). The material was thoroughly dried in vacuo (60°C.).

3.2 g. (0.011 mole) of the product obtained above and 2.7 g. (0.012 mole) of 2,3-dichloro-5,6-dicyano-1,4-benzoquinone were heated in 60 ml. of freshly opened analytical grade dioxane at 60°C. for 24 hours under nitrogen with stirring. The mixture was cooled to room temperature and the hydroquinone (2.05 g.) removed by filtration. The filtrate was concentrated to a volume of 10 ml. in vacuo and an additional 0.4 g. of hydroquinone collected. The product was precipitated by the addition of benzene (60 ml.) to the filtrate. Wgt. = 1.9 g. Concentration of the filtrate to a volume of 20 ml. followed by the addition of benzene furnished an additional 1.0 g. of product.

The hydroquinone collected was compared to and found to be identical with a standard sample of 2,3-dichloro-5,6-dicyano-1,4-hydroquinone substantiating the removal of the two hydrogens from the phthalidyl-substituted carboxyindole to yield a dehydro product under anhydrous conditions. The dehydro product upon initial precipitation was yellow and was observed to become substantially colorless upon standing in the presence of atmospheric moisture. The colorless product formed upon standing on the basis of molecular weight determination was found to correspond to the hydrated form of the dehydro product was evidenced by a difference of 18 in molecular weight. Further studies revealed that a mixture of dehydro and hydrated products can be obtained in the oxidation step when moisture is present, for example, when trace amounts of water is present in the dioxane solvent. Upon further reaction with orthohydroxyphenylindole following step 3 of Example 1, the dehydro and hydrated intermediates showed substantially equivalent reactivity in the formation of the complete dye.

EXAMPLE 2

The product of Example 1 was prepared in the same manner described above except that o-chloranil (0.029 mole) was substituted for dichlorodicyanoquinone as the oxidizing agent.

In addition to the above, the specific indicator dyes of formulae (1) to (19) and (48) also also were prepared in accordance with the procedure of Example 1. The dye of formula (1) was prepared by reacting indole with the acid, oxidizing the intermediate thus formed and then reacting the oxidized intermediate with orthohydroxyphenyl indole. In preparing the dyes of formulae (2) to (9), the respective 5-substituted indoles were initially reacted with the acid and in preparing the dyes of formulae (16) to (19), the respective 7-substituted indoles were intially reacted with the acid. The dyes of formulae (10) to (15) and (48) were prepared by reacting 7-carboxyindole with the acid and subsequently reacting the intermediate after oxidation with the compound selected for the second aromatic nucleus.

As discussed above, the subject protonated compounds may be prepared by reacting the dehydro and/or the hydrated compounds of formulae II and III with a protic acid. In the preparation of indicator dyes according to the sequence detailed above, the protonated compounds may be produced in situ in the condensation of step 3 as in the foregoing Examples. Alternately, the protonated compounds may be produced prior to condensation with the selected aromatic compound to yield the dye product. The conversion of dehydro and hydrated compounds to the corresponding protonated compound prior to condensation was carried out as follows:

Approximately 1.0 m. mole of (7-carboxyindol-3-yl) dehydronaphthalide was added to 5.0 ml. of glacial acetic acid, and the resulting solution, which was substantially colorless, was heated to 70°C. To the heated solution was added 5 ml. of 12% toluene-p-sulfonic acid-acetic acid over a period of about 5 minutes. Upon the addition of the sulfonic acid, the solution turned an intense orange. Upon the subsequent addition of about 1.0 m. mole of 7-hexadecylsulfonamidoindole, the solution turned an intense purple color.

The foregoing procedure was repeated except that a hydrated compound, 3-hydroxy-3-(7-carboxyindol-3-yl) naphthalide, was substituted for the dehydronaphthalide. The 3-hydroxy-naphthalide in glacial acetic acid gave a substantially colorless solution which remained colorless until the toluene-p-sulfonic acid-acetic acid was added whereupon the solution turned an intense orange. The solution changed to an intense purple upon the subsequent addition of the 7-hexadecylsulfonamidoindole.

In a further experiment, a solution of 3-(7-carboxyindol-3-yl)dehydronaphthalide, about 1.0 m. mole in 5 ml. of glacial acetic, was heated at 70°C. (without the addition of toluene-p-sulfonic acid) for about 5 minutes. During this time, the solution did not change in color but remained substantially colorless. To the solution was added about 1.0 m. mole of 7-hexadecylsulfonamidoindole, and heating was continued for about 15 minutes during which time little purplish color was noted. Upon the addition of 5 ml. of 12% toluene-p-sulfonic acid-glacial acetic acid, the solution rapidly turned to an intense purple. This procedure, when repeated with the hydrated compound, 3-hydroxy-3-(7-carboxyindol-3-yl)naphthalide, gave the same results.

As will be apparent from the above experiments, both the dehydro and hydrated compounds of formulae II and III are converted to the corresponding protonated compound, namely, the hydrotosylate, upon the addition of toluene-p-sulfonic acid as evidenced by the color change of the reaction solution from substantially colorless to intense orange. This shift in color towards red together with the intensity of the color indicates a reaction between the dehydro or hydrated compound and the protic acid to form a new species as expected for the formation of cationic species, i.e., a structure as set out in formula (A). The protonated compound may be isolated from the orange reaction solution by removing the glacial acetic acid. In preparing indicator dyes, it is more convenient to use the solution of protonated compound in the subsequent condensation reaction rather than isolating the protonated compound and redissolving it. Forming the protonated compound in situ during the condensation reaction is still more convenient because it does not require an additional step in the overall procedure.

It is also apparent from the above experiments that the rate of the condensation reaction depends upon the acid, i.e., on the conversion of dehydro and hydrated compound to the more reactive protonated compound as evidenced by the more rapid formation of purple color characteristic of the indole naphthalide indicator dye product. Only slight formation of purplish color was observed in the reaction of the dehydro and hydrated naphthalides with the sulfonamidoindole in refluxing glacial acetic acid in the absence of the sulfonic acid. Upon the addition of the sulfonic acid, a rapid change in color to intense purple was observed indicating the more rapid formation of indicator dye product.

Typically, the dehydro indole compounds of formula II are yellowish or slightly pink and give a substantially colorless solution in glacial acetic acid, and the hydrated indole compounds of formula III are white or colorless and also give a substantially colorless solution in glacial acetic acid.

The above experiments were repeated with 3-hydroxy-3-(5-methoxyindol-3-yl)phthalide and the corresponding dehydro compound and gave the same results, namely, the color shift to an intense orange in glacial acetic acid upon the addition of toluene-p-sulfonic acid and the more rapid formation of purple color in glacial acetic acid containing the 7-sulfonamidoindole upon the addition of toluene-p-sulfonic acid.

As noted previously, solvents other than those specified may be usd in the oxidation and the initial and final condensation steps and other acid condensation catalysts may be employed. Though it is not essential, any one or all of the steps of the process may be carried out in an inert atmosphere, for example, under nitrogen, and final indicator dyes may be purified by recrystallization from any appropriate solvent or in any other suitable and convenient manner.

Indicator dyes comprising phthaleins containing an indole radical and a second radical derived from a different N-heterocyclic aryl compound and phthaleins containing an indole radical and a second radical derived from a hydroxy-substituted carbocyclic aryl compound form the subject matter of copending U.S. patent application Ser. No. 464,995, a continuation-in-part of application Ser. No. 202,555, now U.S. Pat. No. 3,816,120 and copending U.S. patent application Ser. No. 456,869, a continuation-in-part of application Ser. No. 202,558, now U.S. Pat. No. 3,816,124, 202,558, respectively. Indicator dyes containing a naphthalide ring-closing moiety substituted in the 6-position with certain groups, such as sulfonamido, form the subject matter of copending U.S. patent application Ser. No. 193,746. 451,077, now U.S. Pat. No. 3,892,778, a continuation-in-part of application Ser. No. 193,746, now U.S. Pat. No. 3,811,881. Phthaleins derived from azaphenanthrol form the subject matter of copending U.S. patent application Ser. No. 398,195, a division of application Ser. No. 177,513, now U.S. Pat. No. 3,779,754. Phthaleins containing one phenol radical and a second carbocyclic aryl radical, which is different, e.g., a phenyl radical with a different p-substituent form the subject matter of copending U.S. patent application Ser. No. 203,544, now U.S. Pat. No. 3,782,937.

The indicator dyes produced in accordance with the present invention may be employed in conventional analytical procedures where phthalein indicator dyes are commonly used, for example, to measure changes in pH value. The dyes produced according to the present invention also find other uses.

As discussed in copending U.S. patent applications, Ser. No. 108,260 and Ser. No. 103,392, now U.S. Pat. Nos. 3,702,244 and 3,702,245, respectively, it has been found that a selectively exposed photosensitive material having a latent image therein may be processed in the presence of extraneous incident radiation actinic thereto by reason of the protection afforded by suitably positioning with respect to the exposure surface of the photosensitive layer an effective concentration of a selected dye or dyes as optical filter agents. The use of certain indole dyes including indole phthalides and naphthalides as optical filter agents for protecting photosensitive materials from radiation in the shorter wavelength region of the visible spectrum forms the subject matter of aforementioned U.S. patent application Ser. No. 108,260. The use of certain dyes derived from phenols and naphthols including phenol and naphthol phthalides and naphthalides as optical filter agents for protecting photosensitive materials from radiation in the longer wavelength region of the visible spectrum forms the subject matter of aforementioned U.S. patent application Ser. No. 103,392.

Indicator dyes found particularly useful as optical filter agents that may be prepared according to the present invention are phthaleins derived from certain hydroxy-substituted carbocyclic and N-heterocyclic compounds which contain a hydrogen-bonding group, i.e., a substituent capable of forming a hydrogen-bonded ring with the respective phenolic —OH and —NH— portions of these compounds. Particular phthaleins of this type derived from phenols and 1-naphthols form the subject matter of copending U.S. patent applications Ser. Nos. 103,864 and 103,865, respectively, now U.S. Pat. Nos. 3,833,615 and 3,833,614, respectively. Particular phthaleins of this type derived from indoles form the subject matter of copending U.S. patent application Ser. No. 409,012, a continuation-in-part of application Ser. No. 108,277, now abandoned. Indoles substituted with selected hydrogen-bonding groups useful in the synthesis of such indole phthalides and naphthalides form the subject matter of copending U.S. patent application Ser. No. 108,663, now U.S. Pat. No. 3,772,329.

Since certain changes may be made in the above products without departing from the scope of the invention herein involved, it is intended that all matter contained in the above description shall be interpreted as illustrative and not in a limiting sense.

What is claimed is:

1. A compound of the formula

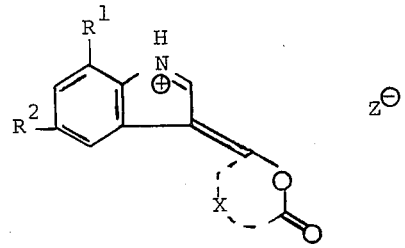

wherein $R^1$ is hydrogen, methoxy, carboxy, —NHSO$_2$R wherein R is selected from alkyl having 1 to 18 carbon atoms and phenyl substituted with alkyl wherein said alkyl substituent has 1 to 18 carbon atoms or —SO$_2$NHR wherein R has the same meaning given above; $R^2$ is hydrogen, alkoxy containing 1 to 12 carbon atoms, carboxy or cyano; X represents the atoms necessary to complete a ring-closing moiety selected from phthalide and naphthalide; an Z is an anion derived from a protic acid having a pKa less than 4 selected from toluene-para-sulfonic acid and sulfuric acid, at least one of said $R^1$ and $R^2$ being hydrogen.

2. A compound as defined in claim 1 wherein said protic acid is toluene-para-sulfonic acid.

3. A compound as defined in claim 1 wherein X represents the atoms necessary to complete naphthalide.

4. The compound

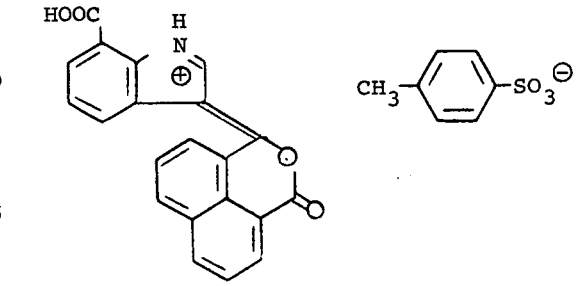

5. The compound

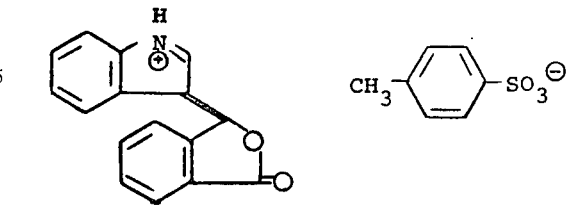

6. The compound
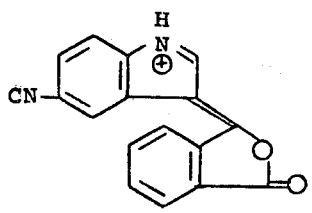 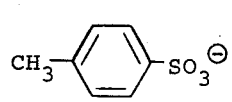
7. The compound
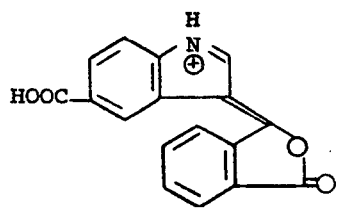 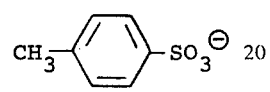
8. The compound
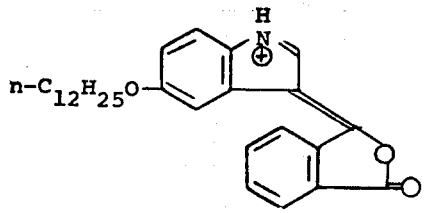
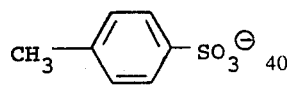
9. The compound
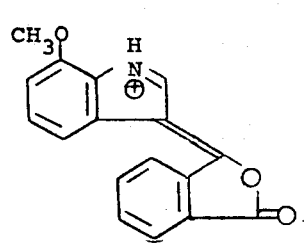 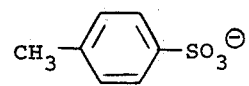
10. The compound
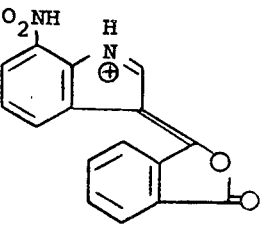
11. The compound
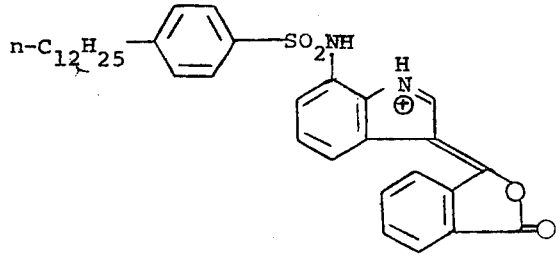
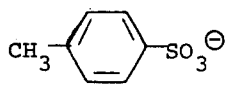
12. The compound
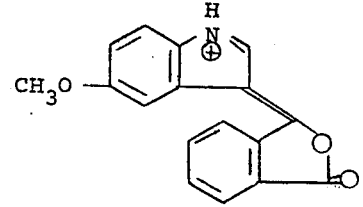
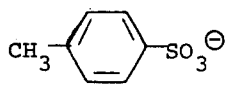 .
* * * * *